United States Patent [19]

Neustadt et al.

[11] Patent Number: 5,298,492

[45] Date of Patent: Mar. 29, 1994

[54] DIAMINO ACID DERIVATIVES AS ANTIHYPERTENSIVES

[75] Inventors: Bernard R. Neustadt, West Orange; Elizabeth M. Smith, Verona; Deen Tulshian, Rockaway, all of N.J.

[73] Assignee: Schering Corporation, Kenilworth, N.J.

[21] Appl. No.: 925,338

[22] Filed: Aug. 4, 1992

[51] Int. Cl.$^5$ ............................................. A61K 31/17
[52] U.S. Cl. ...................................... 514/19; 514/18; 530/331; 530/332
[58] Field of Search .................. 530/329, 330; 514/17, 514/18, 19

[56] References Cited

U.S. PATENT DOCUMENTS

| | | | |
|---|---|---|---|
| 4,431,644 | 2/1984 | Smith et al. | 424/246 |
| 4,511,504 | 4/1985 | McCullagh | 260/112.5 |

FOREIGN PATENT DOCUMENTS

| | | | |
|---|---|---|---|
| 274234 | 12/1987 | European Pat. Off. | C07C 103/737 |
| 358398 | 8/1989 | European Pat. Off. | C07C 237/20 |
| 474553 | 9/1991 | European Pat. Off. | C07D 207/08 |
| 481522 | 10/1991 | European Pat. Off. | C07D 471/04 |

OTHER PUBLICATIONS

Erdös, *Hypertension*, 16, 4(1990) pp. 363–370.
Johnston, et al, *Am. J. Med.*, 87, (Suppl. 6.) (1989) pp. 24S–28S.
Zimmerman, et al, *Cir. Res.*, 66, 1(1990) pp. 234–240.
Sybertz, et al, *Hypertension*, 15, 2(1990) pp. 152–161.
Sybertz, et al, *J. Pharmacol. Exp. Ther.*, 250, 2(1989) pp. 624–631.
Gros, et al., *Proc. Nat. Acad. Sci.*, 88, (1991) pp. 4210–4214.
Burger, *Medicinal Chemistry*, 1960, pp. 565–581, 600–601.
Cushman et al. Biochemistry 1977, 16 5484.
Stanton et al. *J. Med. Chemn.* 1983, 26, 1267.
Gruenfeld et al. *J. Med. Chem.* 1983, 26, 1277.
Meyer et al. *J. Med. Chem.* 1981, 24, 964.

*Primary Examiner*—Merrell C. Cashion, Jr.
*Assistant Examiner*—David Lukton

*Attorney, Agent, or Firm*—Paul A. Thompson; Anita W. Magatti

[57] ABSTRACT

Novel diamino acid derivative dual inhibitors of neutral endopeptidase and angiotensin converting enzyme of the formula

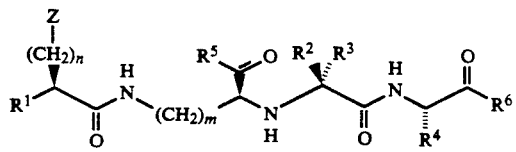

wherein:

Z is amino, lower alkylamino, di-(lower alkyl)amino $R^9C(O)NH$— or an optionally substituted guanidino group;

$R^1$ is hydrogen or $R^7R^8N$—;

$R^2$ is hydrogen, lower alkyl, cyclolower alkyl, aryl-lower alkyl or heteroaryllower alkyl; and $R^3$ is hydrogen, lower alkyl or cyclolower alkyl; or $R^2$ and $R^3$, together with the carbon to which they are attached, comprise a 3–7 membered carboxyclic ring;

$R^4$ is hydrogen, lower alkyl, aryl lower alkyl or heteroaryllower alkyl;

$R^5$ and $R^6$ are independently hydroxy, lower alkoxy, amino, aryllower alkoxy, lower alkylamino and di-(lower alkyl)amino;

$R^7$ is $R^9C(O)$— or $R^{10}SO_2$—; and $R^8$ is hydrogen, lower alkyl, aryllower alkyl or aryl; or $R^7$ and $R^8$, together with the nitrogen to which they are attached, comprise a 5–7 membered ring;

$R^9$ is lower alkyl, aryllower alkyl, aryl, heteroaryllower alkyl, heteroaryl, lower alkoxy, aryllower alkoxy, amino, alkylamino or dialkylamino;

$R^{10}$ is lower alkyl, aryl lower alkyl, aryl, heteroaryl lower alkyl, amino, lower alkylamino, di-(lower alkyl)amino or heteroaryl;

n is 1, 2, 3, 4 or 5; and m is 1, 2, 3, 4 or 5;

or a pharmaceutically acceptable addition salt thereof, useful in the treatment of cardiovascular disorders, are disclosed.

11 Claims, No Drawings

DIAMINO ACID DERIVATIVES AS ANTIHYPERTENSIVES

BACKGROUND OF THE INVENTION

The present invention relates to α,ω-diamino acid derivatives which are dual inhibitors of neutral endopeptidase and angiotensin converting enzyme, useful in the treatment of cardiovascular disorders.

Cardiovascular disorders which may be treated with compounds of the present invention include hypertension, congestive heart failure and renal insufficiency.

The renin-angiotensin system is a complex hormonal system comprised of a large molecular weight precursor, angiotensinogen, two processing enzymes, renin and angiotensin converting enzyme (ACE), and a vasoactive mediator, angiotensin II (A II). The enzyme renin catalyzes the cleavage of angiotensinogen into the decapeptide angiotensin I (A I), which has minimal biological activity on its own and is converted into the active octapeptide A II by ACE. A II has multiple biological actions on the cardiovascular system, including vasoconstriction, activation of the sympathetic nervous system, stimulation of aldosterone production, antinatriuresis, stimulation of vascular growth and stimulation of cardiac growth. A II functions as a pressor hormone and is involved in the pathophysiology of several forms of hypertension.

Angiotensin converting enzyme (ACE) is a zinc-metalloprotease which converts A I to A II. Inhibitors of this enzyme, which have been widely studied, include the drugs captopril, enalapril, lisinopril and spirapril. Although a major mode of action of ACE inhibitors involves prevention of formation of the vasoconstrictor peptide A II, it has been reported in *Hypertension*, 16, 4 (1990) p. 363-370 that ACE cleaves a variety of peptide substrates, including the vasoactive peptides bradykinin and substance P. Prevention of the degradation of bradykinin by ACE inhibitors has been demonstrated, and the activity of the ACE inhibitors in some conditions has been reported in *Circ. Res.*, 66, 1 (1990) p. 242-248 to be mediated by elevation of bradykinin levels rather than inhibition of A II formation.

Neutral endopeptidase (EC 3.4.24 11; enkephalinase; atriopeptidase; NEP) is a zinc-containing metalloprotease which cleaves a variety of peptide substrates on the amino terminal side of aromatic amino acids. Substrates for this enzyme include, but are not limited to, atrial natriuretic factors (ANF), brain natriuretic peptide, met and leu enkephalin, bradykinin, neurokinin A, and substance P.

Inhibitors of NEP lower blood pressure and exert ANF-like effects such as diuresis and increased cyclic guanosine 3',5'-monophosphate (cGMP) excretion in some forms of experimental hypertension. The antihypertensive action of NEP inhibitors is mediated through ANF because antibodies to ANF will neutralize the reduction in blood pressure.

U.S. Pat. No. 4,749,688 also established the antihypertensive action of NEP inhibitors and that co-administration of an ACE inhibitor and a NEP inhibitor results in a greater reduction of blood pressure than observed with either agent alone. The antihypertensive effect is best manifested under conditions in which the renin angiotensin system is suppressed, as reported by Sybertz et al in *J. Parmacol. Exp. Ther.*, 250, 2 (1989) pp. 624-631 and in *Hypertension*, 15, 2 (1990) pp. 152-161. For example, NEP inhibitors reduce blood pressure effectively in the Desoxy-corticosterone salt (DOCA) hypertensive rat, a volume-dependent, renin-suppressed model of hypertension, but are less effective under conditions in which the renin-angiotensin system is activated, such as in the spontaneously hypertensive rat (SHR) and in the two kidney Goldblatt hypertension model. Studies in the SHR and in the two-kidney Goldblatt hypertension model using a prodrug of the NEP inhibitor N-[2(S)-mercaptomethyl-3-(2-methylphenyl)-propionyl]-methionine in combination with the ACE inhibitor spirapril demonstrated the greater efficacy of the combination compared to either drug alone. However, this interaction was inhibited in SHR which had been nephrectomized, a manipulation which markedly suppresses renin levels.

An explanation of this interactive effect of ACE inhibitors and NEP inhibitors on blood pressure is that suppression of the renin angiotensin system allows for full expression of the ANF-like antihypertensive effect of the NEP inhibitor. A II and ANF exert opposite effects on the cardiovascular system and it has been proposed by Johnston et al in *Am. J. Med.*, 87, (Suppl 6) (1990) p. 24S-28S that these two hormonal systems act to counterbalance one another.

Compounds possessing dual activity as NEP-ACE inhibitors have been reported. European Patent Publication EP 0358398 discloses cycloalkyl-substituted glutaramides of the formula

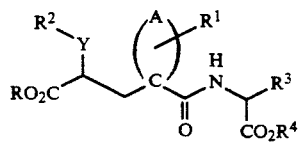

wherein: A completes a 5 or 6 membered carbocyclic ring; $R^1$ is H or alkyl; R and $R^4$ are H, alkyl, cycloalkyl, benzyl or an alternative biolabile ester-forming group; Y is a bond or an alkylene group; $R^2$ is H, aryl, heterocyclyl, or a carboxamido, carbamoyl, sulfamoyl or sulfonamido group; and $R^3$ is a group of the formula

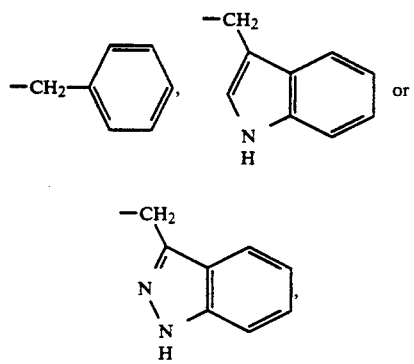

wherein the benzene ring of said group is optionally substituted;

European Patent Publication EP 0474553 discloses actinoin derivatives of the formula

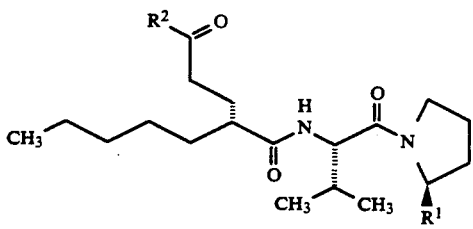

wherein R¹ is sulfoxymethyl, carboxyl, carboxamido, hydroxyaminocarbonyl or alkoxycarbonyl; and R² is hydroxy, alkoxy, hydroxyamino or sulfoxyamino;

European Patent Publication EP 0481522 discloses compounds of the formula

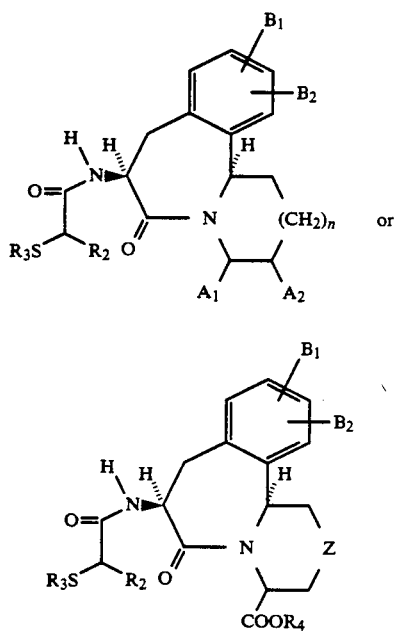

wherein:

A₁ and A₂ are independently H or —COOR₄; provided that where A₁ is H, A₂ is —COOR₄, and where A₁ is —COOR₄, A₂ is H;

B₁ and B₂ are independently H, OH, C₁–C₄ alkoxy, aryl or aryl(C₁–C₄ alkyl); or, where B₁ and B₂ are attached to adjacent carbon atoms, B₁ and B₂ together with the carbons to which they are attached comprise a benzene or methylenedioxy ring;

R₂ is H, C₁–C₈ alkyl, —CH₂—O—(CH₂)₂—O—CH₃, aryl or aryl(C₁–C₄ alkyl);

R₃ is H, acetyl, —CH₂—O—C(O)—CCH₃, or benzoyl;

R₄ is H, —CH₂—O—C(O)—CCH₃, C₁–C₄ alkyl, diphenylmethyl, aryl or aryl(C₁–C₄ alkyl); and n is 0 or 1;

having activity as inhibitors of both neutral endopeptidase and angiotensin converting enzyme; and Gros, et al., *Proc. Natl. Acad. Sci. USA*, 88, (1991) pp 4210–4214, discloses dual inhibitors of ACE and NEP of the formula

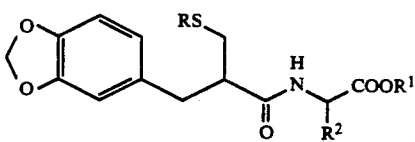

wherein R is H or CH₃C(O)—, R¹ is H or benzyl, and R² is H or methyl.

SUMMARY OF THE INVENTION

Novel compounds of the present invention are represented by the formula I

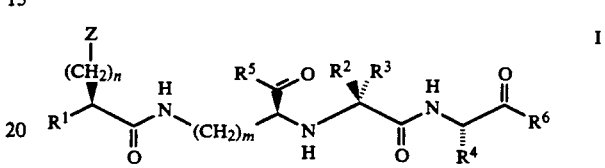

wherein

Z is amino, lower alkylamino, di-(lower alkyl)amino R⁹C(O)NH—, or a guanidino group of the formula R¹¹R¹²NC(=NR¹³)N(R¹⁴)— or R¹¹R¹²NC(NR¹³R¹⁴)=N—, wherein R¹¹, R¹², R¹³ and R¹⁴ are independently hydrogen or alkyl, or wherein R¹¹ and R¹², or R¹³ and R¹⁴, taken together with the nitrogen atom to which they are attached, comprise a 5- or 6-membered ring;

R¹ is hydrogen or a group of the formula R⁷R⁸N—;

R² is hydrogen, lower alkyl, cyclolower alkyl, aryllower alkyl or heteroaryllower alkyl; and R³ is hydrogen, lower alkyl or cyclolower alkyl; or R² and R³, together with the carbon to which they are attached, comprise a 3–7 membered carbocyclic ring;

R⁴ is hydrogen, lower alkyl, aryl lower alkyl or heteroaryllower alkyl;

R⁵ and R⁶ are independently selected from the group consisting of hydroxy, lower alkoxy, amino, aryl-lower alkoxy, lower alkylamino and di(lower alkyl)amino;

R⁷ is R⁹C(O)— or R¹⁰SO₂—; and R⁸ is hydrogen, lower alkyl, aryllower alkyl or aryl; or R⁷ and R⁸, together with the nitrogen to which they are attached, comprise a 5–7 membered ring;

R⁹ is lower alkyl, aryllower alkyl, aryl, heteroaryllower alkyl, heteroaryl, lower alkoxy, aryllower alkoxy, amino, lower alkylamino or di-(lower alkyl)amino;

R¹⁰ is lower alkyl, aryl lower alkyl, aryl, heteroaryl lower alkyl, amino, lower alkylamino, di-(lower alkyl)amino or heteroaryl;

n is 1, 2, 3, 4 or 5;

m is 1, 2, 3, 4 or 5;

or a pharmaceutically acceptable addition salt thereof.

Preferred are compounds of the formula I wherein n is 4 and m is 1. Also preferred are compounds of the formula I wherein R⁴ is 4-hydroxyphenylmethyl. Another group of preferred compounds is that wherein: Z is amino, benzyloxy-C(O)NH— or C₂H₅NHC(=NC₂H₅)NH—. Yet another group of preferred compounds is that wherein R¹ is H or CH₃SO₂NH— and R⁶ is hydroxy, lower alkoxy or aryl-lower alkoxy.

More preferred are compounds of the formula Ia, Ib or Ic:

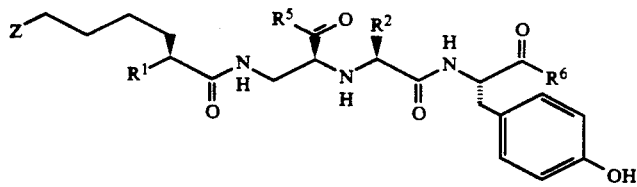

Ia

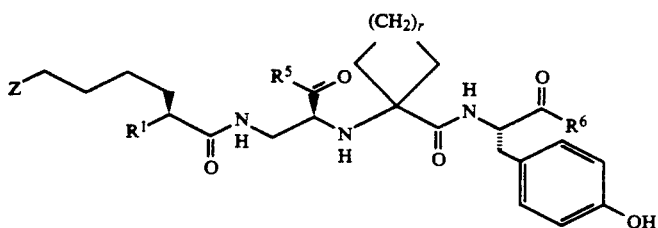

wherein r is 0, 1, 2 or 3

Ib

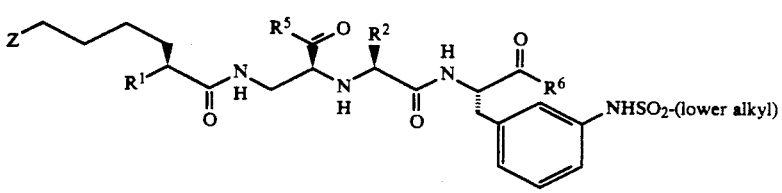

Ic

Especially preferred are compounds of the formula Ia, Ib or Ic, wherein Z is amino, $R^9C(O)NH-$ or $R^{11}R^{12}NC(=NR^{13})N(R^{14})-$; $R^1$ is H or $CH_3SO_2NH-$; $R^2$ is iso-propyl, propyl or benzyl; $R^5$ and $R^6$ are independently hydroxy, lower alkoxy or aryllower alkoxy; $R^9$ is aryllower alkoxy; $R^{11}$ and $R^{13}$ are alkyl; and $R^{12}$ and $R^{14}$ are hydrogen.

The invention also relates to pharmaceutical compositions comprising a compound of the formula I, and to methods of treatment of cardiovascular diseases comprising administering a compound of the formula I to a mammal in need of such treatment.

DETAILED DESCRIPTION

As used herein, the term "lower alkyl" means straight or branched alkyl chains of 1 to 6 carbon atoms, and "lower alkoxy" similarly refers to alkoxy groups having 1 to 6 carbon atoms. Cyclolower alkyl means cyclic alkyl groups of 3 to 6 carbon atoms.

The term "aryl" means a phenyl or naphthyl group substituted by 0-5 substituents independently selected from the group consisting of alkyl, hydroxy, lower alkoxy, lower alkenoxy, lower alkoxycarbonyloxy, lower cycloalkoxycarbonyloxy, lower alkylsulfonamido, arylsulfonamido, halo, trifluoromethyl, phenyl, phenoxy or phenylthio, or wherein two substituents attached to adjacent carbons together comprise a fused 5- or 6-membered ring containing 0 or 1 heteroatoms selected from N, O and S, e.g. dihydrobenzofuranyl, dihydrobenzothienyl, or indanyl.

The term "heteroaryl" means furanyl, thienyl, pyrrolyl, benzofuranyl, benzothienyl, indolyl, indazolyl or pyridyl, substituted by 0-4 substituents independently selected from the group consisting of alkyl, hydroxy, lower alkoxy, lower alkenoxy, lower alkoxycarbonyloxy, lower cycloalkoxycarbonyloxy, lower alkylsulfonamido, arylsulfonamido, halo, trifluoromethyl, phenyl, phenoxy or phenylthio.

The term "halo" means fluorine, chlorine, bromine or iodine radicals.

Certain compounds of the invention are acidic, e.g., those compounds which possess a carboxyl group. These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

The salts may be formed by conventional means, as by reacting the free acid form of the product with one or more equivalents of the appropriate base in a solvent or medium in which the salt is insoluble, or in a solvent such as water which is then removed in vacuo or by freeze-drying or by exchanging the cations of an existing salt for another cation on a suitable ion exchange resin.

Certain compounds of the invention, e.g., those with a basic Z group, also form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of this invention.

Compounds of the formula I may have asymmetrical carbon atoms in addition to those designated and therefore include various stereoisomers. The invention includes all such isomers both in pure form and in admixture, including racemic mixtures.

The following solvents and reagents employed in preparing compounds of the present invention are identified by the abbreviations indicated: diethyl ether (Et$_2$O); ethyl acetate (EtOAc); methanol (MeOH); ethanol (EtOH); dimethylformamide (DMF); tetrahydrofuran (THF); acetic acid (AcOH); 1-(3-dimethylaminopropyl)-3-ethylcarbodiimide hydrochloride (EDCl); dicyclohexylcarbodiimide (DCC); 1-hydroxybenzotriazole hydrate (HOBT); p-toluenesulfonic acid (p-TSA); trifluoroacetic acid (TFA);

Compounds of the present invention can be prepared via methods known to those skilled in the art.

One method of preparing compounds of the formula I is outlined in Scheme A. A N-protected amino acid of the formula II, wherein PG is a protecting group, e.g. benzyloxycarbonyl, is coupled with an amine of the formula III using a dehydrative coupling agent, e.g. EDCl or DCC, and HOBT, in a suitable solvent, such as DMF. The N-protecting group of resulting peptide IV is removed, e.g. in the case of a benzyloxycarbonyl protecting group, by hydrogenation over Pd/C, to form an amine of the formula V. The amine of formula V is then coupled, using known methods, to a carboxylic acid of the formula VI to form a compound of the formula I.

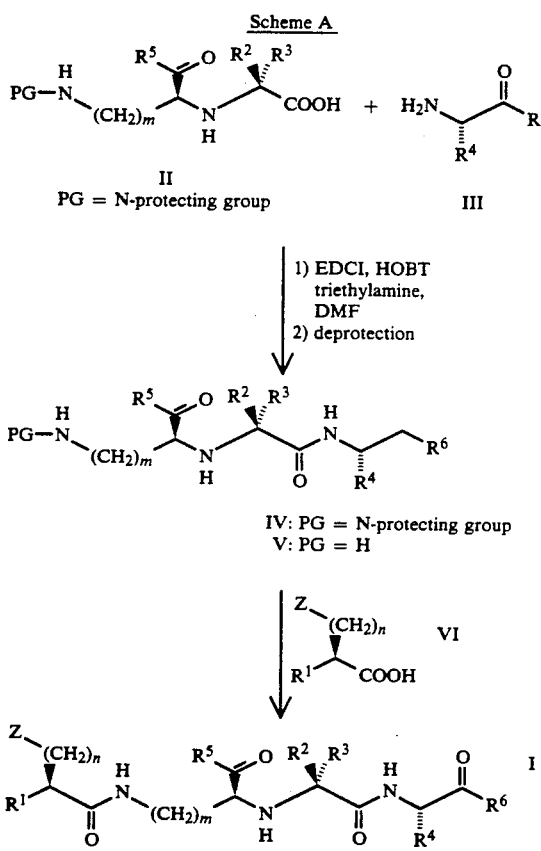

Alternatively, an amine of the formula V can be prepared by coupling an azido carboxylic acid of the formula XXI with an amine of the formula III using a dehydrative coupling agent, e.g. EDCl or DCC, and HOBT, in a suitable solvent, such as DMF. The resulting azido amide is hydrogenated over a suitable catalyst, e.g. Pd on carbon, to give the desired amine.

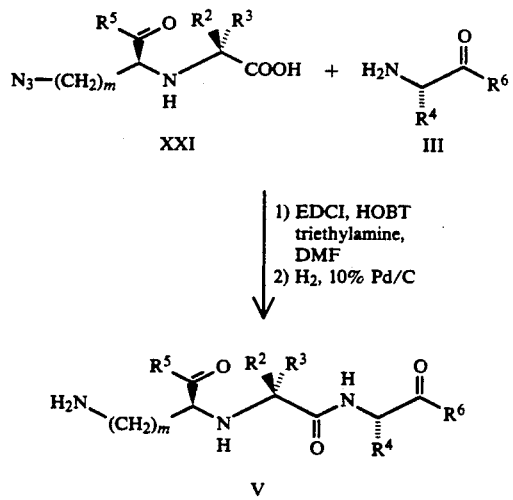

Compounds of the formula II can be prepared by reacting an amine of the formula VII, wherein PG is a protecting group, e.g. benzyloxycarbonyl, with a triflate of the formula VIII, wherein LG is lower alkoxy or aryllower alkoxy. The reaction is carried out in a suitable solvent, e.g., in the presence of a non-nucleophilic strong base, e.g. Proton Sponge ®, giving rise to a compound of the formula IX, wherein LG and PG are as defined above. The C(O)LG ester group of IX is hydrolyzed to give a compound of the formula II, by treating with base, e.g. sodium hydroxide, in a suitable solvent, e.g. methanol, or alternatively treating with acid, e.g. TFA, in a suitable solvent, e.g. CH$_2$Cl$_2$.

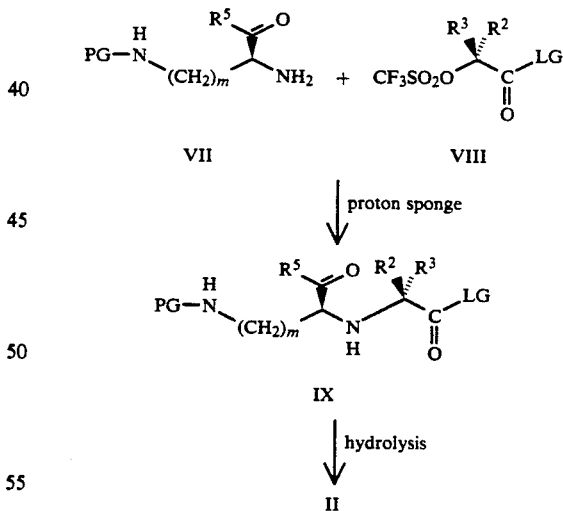

Amines of the formula III are commercially available or can be prepared via known procedures. Where chiral amines of the formula III are not available, they can be separated from racemic amines via known methods. For example, a racemic amine of the formula III, wherein R$^{6a}$ is lower alkoxy, is protected with a suitable N protecting group PG$^a$, e.g. where PG$^a$ is benzyloxycarbonyl, by treatment with benzylchloroformate and a base, such as triethylamine, in a solvent, such as dioxane. The N-protected compound of formula XVIII is hydrolyzed with an aqueous base, such as sodium hydroxide solution, in a suitable solvent, e.g. THF to form a carboxylic acid of the formula XIX. The racemic acid XIX is enantioselectively esterified with an alcohol of the formula $R^{6b}OH$, wherein $R^{6b}$ is lower alkoxy or aryllower alkoxy, e.g. by treating with the alcohol, papain, L-cysteine and 1M citrate buffer, to give a chiral ester of the formula XX. The N-protecting group is removed via known methods, e.g. in the case of N-benzyloxycarbonyl protection, by hydrogenation in a suitable solvent, such as ethanol, in the presence of a palladium catalyst, to produce the corresponding amine of formula III.

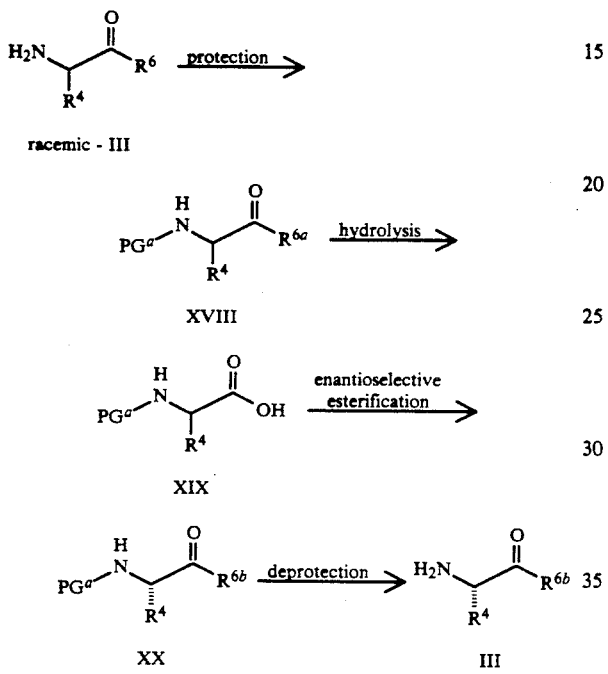

Amines of the formula VII are commercially available or can be prepared by procedures well known in the art. For example, amines of the formula VIIa, wherein $PG^b$ is benzyloxycarbonyl and $R^{5a}$ is hydroxy, lower alkoxy, or aryllower alkoxy can be prepared via the following procedure. A diamino acid X is converted to the N,N'-bis(benzyloxycarbonyl) derivative XI, by treating with benzylchloroformate and a base, e.g. sodium hydroxide, in a suitable solvent, e.g. toluene/water. Compound XI is cyclized to the oxazolidinedione XII, e.g. by heating with thionyl chloride in a suitable solvent, such as $CH_2Cl_2$. The oxazolidinedione XII is then selectively hydrolyzed to the amino acid VIIa, wherein $R^{5b}$ is hydroxy, by treating with acid, e.g. HCl, in an appropriate solvent, e.g. acetone.

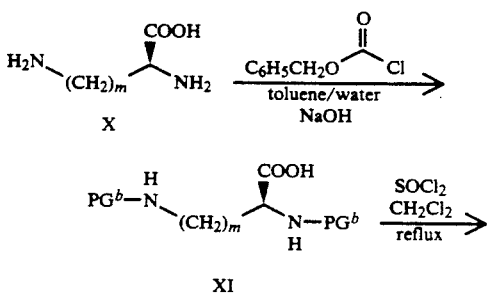

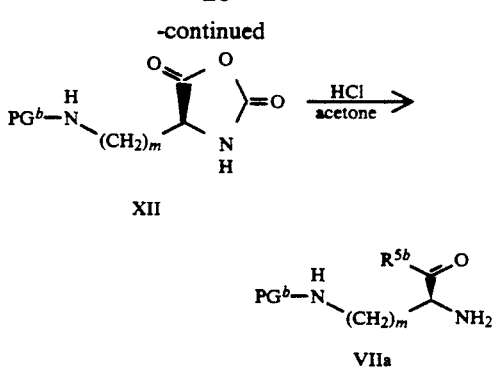

Amines of the formula VIIa, wherein $R^{5b}$ is lower alkoxy, are prepared by reacting an oxazolidinedione of formula XII with an alcohol of formula $R^{5c}H$, wherein $R^{5c}$ is lower alkoxy, and thionyl chloride, in an appropriate solvent, e.g. $CH_2Cl_2$.

Amines of the formula VIIa, wherein $R^{5b}$ is t-butyloxy, are prepared by reacting a solution of an amine of formula VIIa in a suitable solvent, e.g. dioxane, with isobutylene gas in a sealed vessel.

Amines of the formula VIIa, wherein $R^{5b}$ is aryllower alkoxy, are prepared by heating an amine of the formula VIIa with an alcohol of the formula $R^{5d}H$, wherein $R^{5d}$ is aryllower alkoxy, and an acid, e.g. pTSA, in a suitable solvent, e.g. toluene.

Triflates of the formula VIII are prepared by reacting an alcohol of the formula XIII with trifluoromethanesulfonic anhydride and a base, such as pyridine, in a solvent, such as $CH_2Cl_2$.

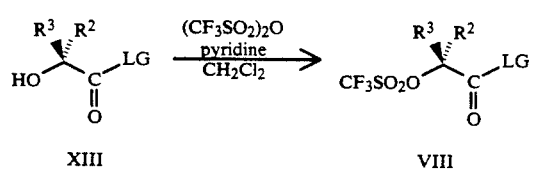

Alcohols of the formula XIII are commercially available or can be prepared via known methods. For example, alcohols of the formula XIII, wherein $LG^a$ is t-butoxy can be prepared from an acetoxypropionic acid XIV. Treating the acid XIV with isobutylene and an acid, such concentrated $H_2SO_4$, in a solvent, such as $CH_2Cl_2$, in a sealed vessel provides the t-butyl ester XV, which is selectively hydrolyzed with diaminoethane in a suitable solvent, such as DMF, to give the alcohol XIII.

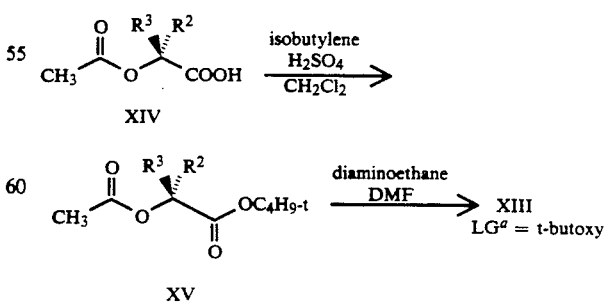

To prepare an alcohol of the formula XIII, wherein $LG^b$ is lower alkoxy or aryllower alkoxy, treat the corresponding hydroxy acid XVI with a lower alkyl halide, e.g. methyl iodide, or a lower arylalkyl halide, e.g. benzyl chloride, in the presence of a suitable base, e.g. cesium carbonate, in a solvent such as DMF.

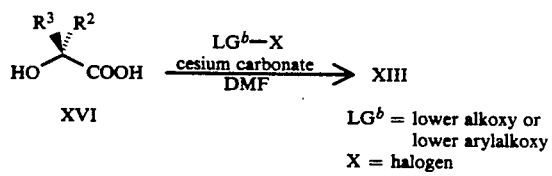

$LG^b$ = lower alkoxy or lower arylalkoxy
X = halogen

Hydroxy acids of the formula XVI are commercially available or can be prepared via known procedures. For example, compounds of the formula XVI can be prepared from amino acids of the formula XVII by treating with H₂SO₄, sodium nitrite and water.

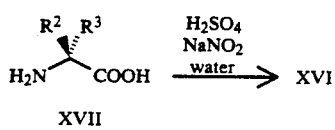

Compounds of the formula XXI (above) can be prepared by reacting an amino ester of the formula XXII with a triflate of the formula XXIII, in the presence of an acid scavenger, such as Proton Sponge ®, followed by hydrolysis of the resulting azido ester XXIV.

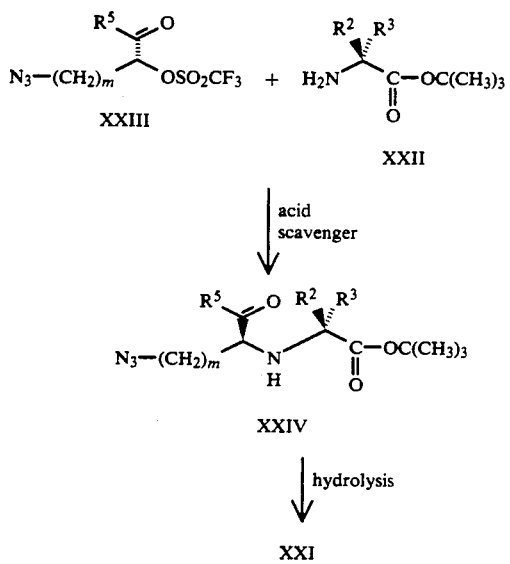

Triflates of the formula XXIII can be prepared from a D-hydroxy acid XXV by esterification of the carboxylic acid to give the diol XXVI. The primary alcohol is selectively converted to the analogous azide XXVII, followed by reaction with triflic anhydride to give the triflate XXIII.

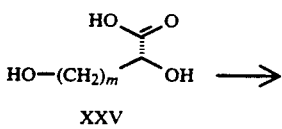

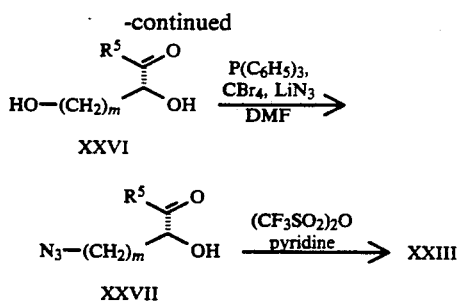

Alternatively, compounds of the formula XXVII, wherein m=1, can be prepared via esterification of (R)-2-hydroxy-3-azidopropionic acid XXVIII. The hydroxy acid XXVIII can be prepared from commercially available 3,4-isopropylidene-D-mannitol via known methods.

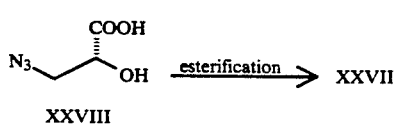

Carboxylic acids of the formula VI, diamino acids of the formula X, acetoxypropionic acids XIV, amino acids of the formula XVII and amino esters of formula XXII are commercially available or can be prepared by methods well known in the art.

The antihypertensive effects of dual inhibitors of the present invention are determined according to the following procedures.

DOCA Salt Model

For the DOCA salt hypertension model, male Sprague Dawley rats weighing 100–150 g are anesthetized with ether and the right kidney is removed. Three pellets containing Doc acetate (desoxycorticosterone acetate, DOCA, 25 mg/pellet) are implanted subcutaneously. Animals recover from surgery, are maintained on normal rat chow and are allowed free access to a fluid of 1% NaCl and 0.2% KCl instead of tap water for a period of 25–30 days. This procedure results in a sustained elevation in blood pressure and is a slight modification of published procedures (e.g. Brock et al, 1982) that have been used to produce DOCA salt hypertension in the rat.

On the day of the study, animals are again anesthetized with ether and the caudal artery is cannulated for blood pressure measurement. Patency of the caudal artery cannula is maintained with a continuous infusion of dextrose in water at a rate of 0.2 mL/hr. Animals are placed into restraining cages where they recover consciousness. Blood pressure is measured from the caudal artery catheter using a Statham pressure transducer attached to a Beckman oscillographic recorder. In addition, a cardiovascular monitoring device (Buxco Eletronics, Inc.) and a digital computer are used to calculate average blood pressures.

After an equilibration period of at least 1.5 hr., animals are dosed subcutaneously (1 mL/kg) with vehicle (methylcellulose, hereinafter MC) and dual NEP-ACE inhibitor, and blood pressure is monitored for the next 4 hours.

ANF Potentiation Model

Male spontaneously hypertensive rats (SHR), 16–18 weeks old, 270–350 g, are anesthetized with ether and the abdominal aorta is cannulated through the tail artery. The animals are then placed into restrainers to recover from anesthesia (in less than 10 min.) and remain inside throughout the experiments. Through a pressure transducer (Gould P23 series) analog blood pressure signals are registered on a Beckman 612 recorder. A Buxco digital computer is used to obtain mean arterial pressures. Patency of the arterial cannula is maintained with a continuous infusion of 5% dextrose at 0.2 mL/hr. Animals are allowed a 90-min equilibration period. The animals first undergo a challenge with an ANF such as atriopeptin II (AP II) or AP28 at 30 μg/kg iv and at the end of 60 min. are treated with drug vehicle or a diamino acid dual inhibitor subcutaneously. A second ANF challenge is administered 15 min. later and blood pressure is monitored for the next 90 min.

AI Challenge Assay

Male Sprague-Dawley rats weighing 270–345 g are anesthetized with ether and the abdominal aorta cannulated via the caudal (ventral tail) artery with polyethylene tubing (PE10 fused to PE50). A jugular vein is also cannulated with polyethylene tubing and both cannulae exteriorized at the back of the neck. The catheters are filled with heparinized saline (0.2%) and sealed. Animals are then returned to their cages and fasted overnight. The next day, place the animals into plastic restrainers. Blood pressure is recorded from the arterial catheter. Patency of the arterial cannula is maintained by a continuous infusion of 5% dextrose in water at a rate of 0.2 mL/hr.

After a 30 min. stabilization period, animals are challenged with angiotensin I (AI) and angiotensin II (AII) (0.3 μg/kg dissolved in physiological saline solution and injected iv in volumes of 100 μL/kg followed by a 100 μL flush) twice at 5–10 min. intervals during a control period. The diamino acids are then administered orally (via a feeding needle) in 0.4% aqueous methylcellulose vehicle in a volume of 2 mL/kg. AI and AII challenges are repeated at 30 min. intervals for the next 6 hr.

FSHR Assay

Male spontaneously hypertensive rats (SHR), 16–18 weeks old, are pretreated via oral gavage with 50 mg/kg of furosemide (in a volume of 4 mL/kg) the evening before the day of testing. The rats were fasted overnight, but had ad libitum access to water, and were pretreated with furosemide (as before) the morning before surgical preparation on the day of testing. The pretreated rats are anesthetized with ether, the caudal (ventral tail) artery cannulated with polyethylene tubing (PE50), and their blood pressure and heart rate recorded. The rats are placed in plastic cages to recover.

After a 90 minute stabilization period, the diamino acids are administered orally as solutions or suspensions in 0.4% aqueous methylcellulose vehicle via a feeding needle. The amino acid or vehicle is given in a volume of 4 mL/kg.

Alternatively, the diamino acids (0.4%) dissolved or suspended in a vehicle composed of 10% (v/v) ethanol, 20% 0.1N (tris[hydroxymethyl]aminoethane) and 70% methylcellulose, are administered via a subcutaneous (sc) route. A volume of 2 mL/kg is used to deliver the drug or vehicle in these sc studies.

ANF has been shown to exert beneficial hemodynamic and renal actions in congestive heart failure (CHF) with the exception of the most severe states, in which its actions may be blunted. ANF and the renin angiotensin system also act as physiological antagonists of one another in CHF. Therefore, it is contemplated that a dual NEP-ACE inhibitor will be useful in the treatment of CHF. Measurements of the degree of diuresis and natriuresis, as well as hemodynamics, are used to determine the efficacy of the present combination in the treatment of CHF.

A variety of pharmaceutical dosage forms are suitable preferably for oral or parenteral administration, although mechanical delivery systems such as transdermal dosage forms are also contemplated.

The daily dosages of the compounds of this invention for treatment of hypertension or congestive heart failure are about 0.3 mg/kg to about 100 mg/kg of mammalian weight per day administered in single or divided doses. The exact dose to be administered is determined by the attending clinician and is dependent on the potency of the compound administered, the age, weight, condition and response of the patient.

Generally, in treating humans having hypertension or congestive heart failure, the compounds of this invention can be administered in dosage ranges of about 1.0 to 50 mg/kg.

Typical oral formulations include tablets, capsules, syrups, elixirs and suspensions. Typical injectable formulations include solutions and suspensions.

The typical pharmaceutically acceptable carriers for use in the formulations described above are exemplified by: sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene glycol polymers; betacyclodextrin; fatty alcohols; and hydrolyzed cereal solids, as well as other non-toxic compatible fillers, binders, disintegrants, buffers, preservatives, antioxidants, lubricants, flavoring agents, and the like commonly used in pharmaceutical formulations.

Following are examples of procedures for preparing compounds of formula I.

PREPARATION 1

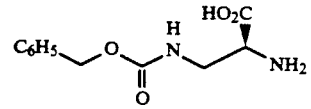

Step A: In an ice-water bath, to 2(S),3-diamino-propionic acid (32 g) in water (1000 mL) add, with stirring, concurrently solutions of benzyl chloroformate (76 mL) in toluene (20 mL) and 4N NaOH (133 mL) over 30 min. Stir at 20°–25° C. for 45 min and then add additional benzyl chloroformate (34 mL) in toluene (10 mL) and 4N NaOH (61 mL) concurrently over 10 min. Stir the mixture at ambient temperature for 2 hr. Add diethyl ether (Et$_2$O) (200 mL) and stir for 10 min. Filter and was the solid with Et$_2$O (200 mL). Extract the aqueous solution with Et$_2$O. Combine the aqueous solution with the solid and add concentrated HCl to pH 1–2. Extract the aqueous solution with EtOAc (250 mL twice). Dry the EtOAc extract (MgSO$_4$) then concentrate in vacuo to give 2(S),3-bis-(benzyloxycarbonylamino)propionic acid, $[\alpha]^{23.6}_D = -13.7°$ (MeOH).

Step B: Suspend the product of Step A (2 g) in CH$_2$Cl$_2$ (25 mL) and treat with thionyl chloride (1.6 mL). Stir the resulting mixture at room temperature for 1 hr and then heat under reflux for 1.5 hr. Concentrate the mixture in vacuo and triturate with hexane (3 times). Dissolve the residue in CH$_2$Cl$_2$ (10 mL), treat with hexane (30 mL), and stir overnight. Filter to give 4(S)-benzyloxycarbonylaminomethyl-2,5-oxazolidinedione.

Step C: Treat the product from Step B (11 g) in acetone (75 mL) with 6N HCl (90 mL) and stir at room temperature for 2 days. Remove the acetone in vacuo and wash the aqueous mixture with Et$_2$O, twice. Treat the aqueous solution with concentrated NH$_4$OH to pH 5 to give a precipitate, m.p. 218°-228° C. Heat a portion of the precipitate (0.6 g) with 50% MeOH/H$_2$O (30 mL), boil down to 20 mL, filter, and leave at room temperature and filter to give the title compound, m.p. 231°-2° C.

For preparation of the racemic compound, see: S. Takagi, Chem. Pharm. Bull. Japan, 7, 616 (1959).

PREPARATION 2

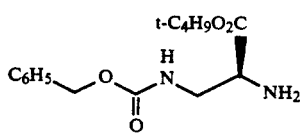

Add the product of Preparation 1 (2.5 g) to dioxane (100 mL), then add 0.5 mL of H$_2$SO$_4$, stir and cool to −20° C. Treat with isobutylene gas (25 mL), seal the reaction vessel, and stir at room temperature for 3 days. Vent the reaction vessel, dilute with Et$_2$O (100 mL) and 7% NaOH (50 mL). Dry the Et$_2$O solution over MgSO$_4$, then concentrate in vacuo to give the title compound.

PREPARATION 3

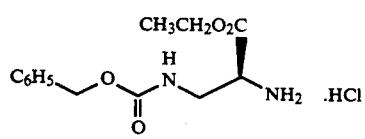

Add EtOH (2.0 mL) to a solution of the oxazolidinedione from Preparation 1, Step B (1.0 g) in CH$_2$Cl$_2$ (12 mL) and thionyl chloride (0.8 mL), and heat the solution under reflux for 1 hr. Concentrate the mixture in vacuo, triturate with Et$_2$O, and filter to give a white solid. Recrystallize from CH$_3$CN to give the title compound, m.p. 163°-5° C., $[\alpha]^{23.6}_D = -9.5°$ (MeOH).

PREPARATION 4

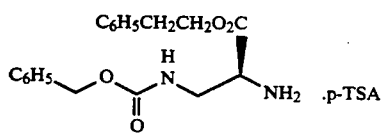

Heat, in the presence of a Dean-Stark trap, the product of Preparation 1 (6.6 g), phenethyl alcohol (26 mL), and p-TSA (5.5 g) in toluene (60 mL) overnight. Cool and add Et$_2$O (100 mL), then collect the solid and recrystallize from MeOH/Et$_2$O to give the title compound, m.p. 134°-6° C., $[\alpha]^{22.5}_D = -9.2°$ (MeOH).

PREPARATION 5

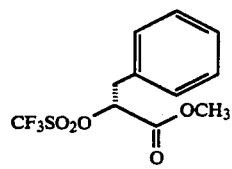

Cool trifluoromethanesulfonic anhydride (1.5 mL) in CH$_2$Cl$_2$ (20 mL) to −20° to −30° C. Add pyridine (0.7 mL) and stir to give a precipitate. Add 3-phenyl-2(R)-hydroxypropionic acid methyl ester (1.3 g) in CH$_2$Cl$_2$ (10 mL). Adjust pH if necessary with pyridine. Warm the mixture to 0°-10° C., add excess 1N HCl, stir 5 min., then add Et$_2$O (60 mL). Extract the Et$_2$O solution with water, 1N NaHCO$_3$, and again with water. Dry the Et$_2$O solution (MgSO$_4$), then concentrate in vacuo to give the title compound.

Using the appropriate starting hydroxy esters, the following compounds can be prepared via substantially the same procedure:

Prep5a

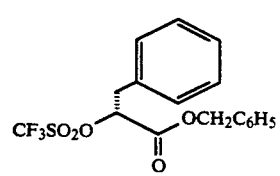

Prep5b

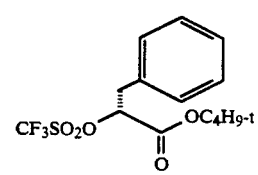

Prep5c

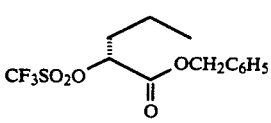

Prep5d

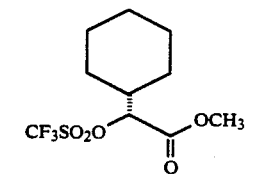

PREPARATION 6

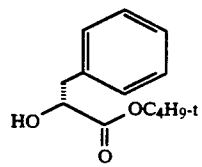

Step A: Cool to −30° to −20° C., 3-phenyl-2(R)-acetoxypropionic acid (10.5 g) in CH$_2$Cl$_2$ (200 mL), add conc. H$_2$SO$_4$ (0.5 mL) and isobutylene (120 mL), seal the vessel, and stir at room temperature for 2 days. Vent the vessel, pour the reaction mixture into NaHCO₃ solution, and extract with CH₂Cl₂. Dry the CH₂Cl₂ extract (MgSO₄), then concentrate in vacuo to give 3-phenyl-2(R)-acetoxypropionic acid t-butyl ester.

Step B: Under anhydrous conditions, heat the product of Step A (7.50 g) with diaminoethane (1.28 g) in DMF (17 mL) at 50°-53° C. for 22 hr. Dilute with Et₂O, wash with 10% KHSO₄ solution, and then water. Concentrate the dried (MgSO₄) solution in vacuo to a residue. Chromatograph the residue on silica gel (40μ, 500 mL) using CH₂Cl₂ as eluant, to give the title compound, $[\alpha]^{26}_D = -11.9°$ (MeOH).

PREPARATION 7

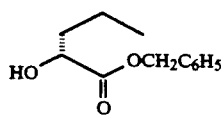

Step A: Cool D-norvaline (20.0 g) in 5% H₂SO₄ (360 mL) to 0°-5° C. and treat with sodium nitrite (30 g) in water (140 mL) dropwise over 1 hr. Warm the resulting mixture to room temperature and stir for 20 hr. Extract with Et₂O (3×400 mL). Concentrate the dried (MgSO₄) Et₂O solution in vacuo to give 2(R)-hydroxyvaleric acid, $[\alpha]^{26}_D = +8.4°$ (MeOH).

Step B: Treat 2(R)-hydroxyvaleric acid (10.22 g), from Step A, in DMF (70 mL) at 0°-5° C. with benzyl chloride (9.6 mL) and cesium carbonate (27.3 g), warm to room temperature, and stir for 18 hr. Concentrate the reaction mixture in vacuo and partition between water and EtOAc. Concentrate the dried (MgSO₄) EtOAc solution in vacuo to a residue. Chromatograph the residue on a column of flash silica gel (40μ, 1600 mL) using CH₂Cl₂ as eluant to give the title compound.

PREPARATION 8

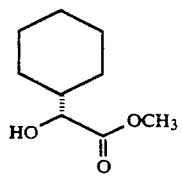

Treat 2(R)-hydroxycyclohexylacetic acid (23.00 g) in DMF (125 mL) at 0°-5° C. with methyl iodide (17.0 mL) and cesium carbonate (47.4 g), warm to room temperature, and stir for 18 hr. Concentrate the reaction mixture in vacuo and partition between water and Et₂O. Concentrate the dried (MgSO₄) Et₂O in vacuo to give an oil. Chromatograph this oil on a column of flash silica gel (40μ, 2000 mL) using CH₂Cl₂ as eluant to give the title compound.

PREPARATION 9

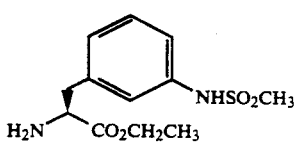

Step A: At 10°-15° C., add benzylchloroformate (15.5 mL) dropwise to a heterogeneous mixture of 3-methanesulfonamido-D,L-phenylalanine ethyl ester (25.00 g) and triethylamine (15 mL) in dioxane (400 mL). Warm to room temperature, stir overnight, and remove the dioxane in vacuo. Partition the mixture between EtOAc (200 mL)/water (500 mL). Wash the EtOAc solution with water (500 mL), 1N HCl (500 mL), 5% NaHCO₃ (500 mL), and brine (500 mL). Concentrate the dried (MgSO₄) EtOAc solution in vacuo to a residue. Chromatograph the residue on silica gel (40μ, 2200 mL) using EtOAc:hexane (3:7) as eluant to give N-benzyloxycarbonyl-3-methanesulfonamido-D,L-phenylalanine ethyl ester.

Step B: Add 1N NaOH (107 mL) to the product of Step A (14.80 g) in THF (100 mL) and stir overnight. Concentrate the THF solution in vacuo and partition between EtOAc (700 mL)/2N HCl (200 mL). Concentrate the dried (MgSO₄) EtOAc solution in vacuo to a residue. Add CH₂Cl₂ (50 mL) and concentrate in vacuo (3 times) to give N-benzyloxycarbonyl-3-methanesulfonamido-D,L-phenylalanine.

Step C: Treat the product of Step B (12.5 g) in EtOH (400 mL) with papain (2.56 g freshly ground), L-cysteine (0.156 g) and freshly made 1M citrate buffer pH 4.5 (2.8 mL). After 2 hr, add papain (1.28 g), L-cysteine (0.078 g), and 1M citrate buffer pH 4.5 (1.4 mL). Repeat the latter addition of papain, L-cystein, and citrate buffer at 4 and 6 hr intervals. Stir the resulting mixture for 4 days. Filter, wash with EtOH, and concentrate in vacuo to a residue. Partition the residue between Et₂O (1400 mL)/5% NaHCO₃ (6×150 mL). Concentrate the dried (MgSO₄) Et₂O solution in vacuo to give N-benzyloxycarbonyl-3-methanesulfonamido-L-phenylalanine ethyl ester, $[\alpha]^{26}_D = -6.7°$ (MeOH).

Step D: Hydrogenate the product of Step C (5.20 g) in EtOH (300 mL) in the presence of 10% Pd/C (2.1 g) for 5 hr at 50 psi. Filter and wash with CH₂Cl₂. Concentrate the EtOH-CH₂Cl₂ solution in vacuo to give the title compound, $[\alpha]^{26}_D = +14.3°$ (MeOH).

PREPARATION 10

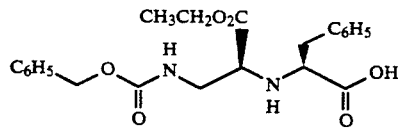

Step A: At 0°-5° C., treat the product of Preparation 3 (liberated from the respective HCl salt (9.6 g) with NH₄OH) in CH₂Cl₂ (90 mL) with Proton Sponge® (9.0 g) and the product Prep 5b of Preparation 5 (12.0 g) in CH₂Cl₂ (75 mL) as described in Example 1A to give a residue. Chromatograph the residue on silica gel (40μ, 1,300 mL) using 0.5:99.5 MeOH:CH₂Cl₂ as eluant to give the product

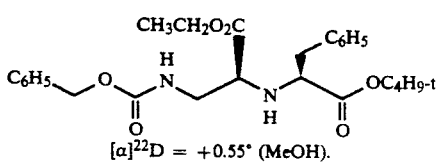

$[\alpha]^{22}D = +0.55°$ (MeOH).

Using substantially the same procedure, the following compound can also be prepared

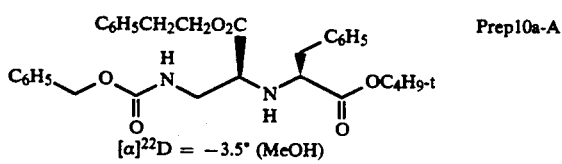

Prep10a-A $[\alpha]^{22}D = -3.5°$ (MeOH)

Step B: Treat the product of Step A (9.2 g) in CH$_2$Cl$_2$ (30 mL) with TFA (30 mL) at room temperature for 5 hr. Concentrate in vacuo. Add Et$_2$O and concentrate in vacuo. Triturate with hexane, decant and concentrate in vacuo to a residue. Chromatograph the residue on silica gel (40μ, 1,100 mL) using CH$_2$Cl$_2$:MeOH:AcOH 310:10:1 to give the title compound, $[\alpha]^{24.5}{}_D = +0.67°$ (MeOH).

Using substantially the same procedure, the following compound can also be prepared

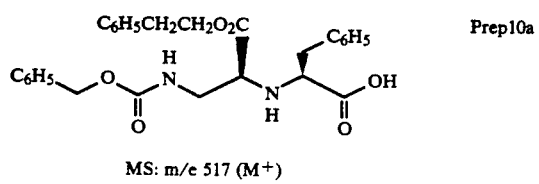

Prep10a

MS: m/e 517 (M$^+$)

PREPARATION 11

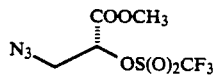

Step A

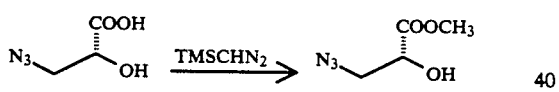

Treat a cold solution of 5.0 g (R)-2-hydroxy-3-azido-propanoic acid in 80 mL of methanol/benzene (7:1) with an excess of trimethylsilyldiazomethane. Neutralize the excess diazomethane with acetic acid, then concentrate the mixture to a residue. Chromatograph the residue on silica gel (30% ethyl acetate/hexane) to give the analogous hydroxy ester. $^1$H NMR (200 MHz, CDCl$_3$): 4.40 (dd, 1H); 3.85 (s, 3H); 3.66–3.50 (ABq, $J_{AB}=12.8$ Hz, $J_{Aq}=4.20$ Hz, $J_{Bq}=3.20$ Hz, 2H).

Step B

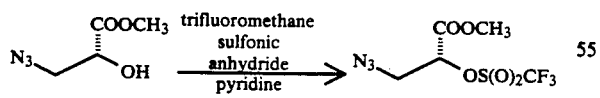

The product of step A (5.0 g) is dissolved in 80 mL of CH$_2$Cl$_2$ and 3.7 mL of pyridine, then cooled to $-25°$ C. Stir the mixture under N$_2$ atmosphere and add 8 mL of trifluoromethanesulfonic anhydride. After ½ h., warm the mixture to 0° to 10° C. Add an excess of 1N HCl, stir for 5 min., then extract with 200 mL of diethyl ether. Wash the organic extract with water, 1N NaHCO$_3$, then again with water. Dry the organic solution over MgSO$_4$, filter and concentrate to give the title compound.

PREPARATION 12

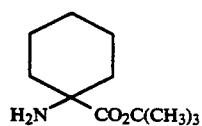

Combine 1-amino-1-cyclohexanecarboxylic acid (10.0 g), t-butyl acetate (140 mL) and HClO$_4$ (6 mL) in a sealed vessel and stir at room temperature for 2 days. Vent the vessel, pour the mixture into aqueous NaHCO$_3$ and extract with EtOAc. Dry the EtOAc extract over MgSO$_4$, filter, and concentrate in vacuo to give the title compound, FAB MS (M+H) 200.

Using substantially the same procedure, the following compounds can be prepared:

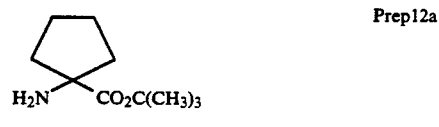

Prep12a

FAB MS (M + H) 186

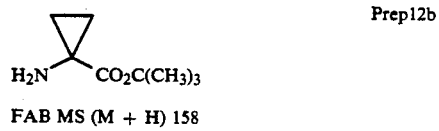

Prep12b

FAB MS (M + H) 158

PREPARATION 13

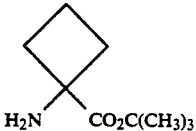

Step A: Heat a solution of cyclobutanecarboxylic acid (4 g) in toluene (60 mL) to 80° C., and add N,N-dimethylformamide di-t-butylacetal (25.0 g), dropwise. Heat the mixture for 1 h., then cool and wash successively with water, aqueous NaHCO$_3$ and brine. Dry over MgSO$_4$, filter, and distill off the toluene to a residue. Chromatograph the residue to give the product

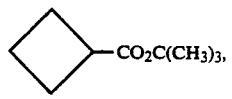

$^1$H NMR (CDCl$_3$) 3.0 (quintet, 1H), 2.05–2.25 (m, 4H), 1.75–1.95 (m, 2), 1.4 (s, 9H).

Step B: Add a solution of the product of step A (2.2 g) in THF (5 mL) to LDA at $-78°$ C. and stir for 1 h at $-78°$ C. Add a solution of triisopropylphenylsulfonyl azide (4.4 g) in THF (15 mL) and stir at $-78°$ C. for 6 h. Quench with AcOH (2.0 mL) at $-70°$ C., warm to room temperature and stir for 1.5 h. Dilute the mixture with CH$_2$Cl$_2$ (200 mL), wash with aqueous NaHCO$_3$, then with brine, dry over MgSO$_4$, filter, and concentrate to a residue. Chromatograph the residue to give the azide product

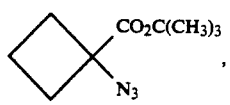

$^1$H NMR (CDCl$_3$) 2.6 (m, 2H), 2.1–2.3 (m, 2H), 1.75–2.05 (m, 2H), 1.5 (s, 9H).

Step C: Hydrogenate the product of step B (2.7 g) in MeOH (50 mL) over 10% Pd on carbon (0.5 g) for 3 h. at 60 psi. Filter and concentrate to give the title compound, $^1$H NMR (CDCl$_3$) 2.4–2.6 (m, 2H), 1.8–2.3 (m, 4H), 1.5 (s, 9H).

PREPARATION 14

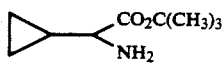

Step A: Add a solution of cyclopropane carboxaldehyde (10 g) in concentrated aqueous NH$_4$OH (22 mL) to a mixture of NH$_4$Cl (8.5 g) and KCN (9.5 g) in water (60 mL) at 0° C., and warm to room temperature. Add Et$_2$O (200 mL) and stir at room temperature for 30 h. Add 200 mL more Et$_2$O and continue stirring for 15 h. Separate the organic layer and concentrate to a residue which is extracted with CH$_2$Cl$_2$ to give the product

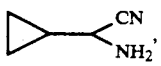

IR 2100 cm$^{-1}$ (CN).

Step B: Heat the product of step A (13 g) and 6N HCl (80 mL) at reflux for 16h. Cool to room temperature and concentrate to a residue. Heat the residue in ethanol (200 mL) at reflux for 2 h., cool to room temperature and filter. Concentrate the filtrate, add water and NH$_4$OH and stir for 0.5 h. Concentrate, treat with Et$_2$O and filter to give the product

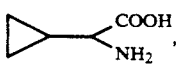

FAB MS (M+H) 116.

Step C: Treat the product of step B (10.0 g) according to the procedure of Preparation 1, step A, to give the product

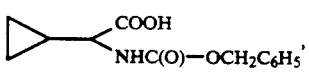

$^1$H NMR (CDCl$_3$) 7.3 (m, 5H), 5.3 (br d, 2H), 3.8 (t, 1H), 1.0–1.2 (m, 1H), 0.3–0.7 (m, 4H).

Step D: Treat the product of step C (10.0 g) according to the procedure of Preparation 13, step A, to give the product

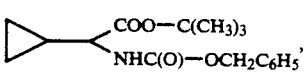

$^1$H NMR (CDCl$_3$) 7.35 (br s, 5H), 5.3 (br d, 2H), 3.75 (t, 1H), 1.45 (s, 9H), 0.9–1.2 (m, 1H), 0.4–0.6 (m, 4H).

Step E: Hydrogenate the product of step D (8.0 g) in MeOH over 10% Pd on carbon at 60 pri for 3 h. Filter, concentrate to a residue and chromatograph the residue (silica gel, 3% MeOH in CH$_2$Cl$_2$) to give the title compound, $^1$H NMR (CDCl$_3$) 2.80 (d, 1H), 1.6–1.75 (br s, 1H), 1.45 (s, 9H), 0.8–1.0 (m, 1H), 0.2–0.6 (m, 4H).

EXAMPLE 1

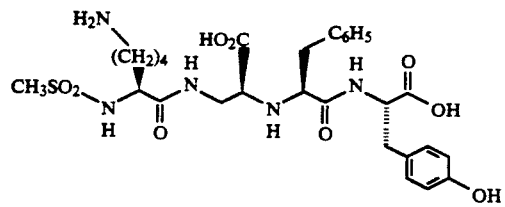

Step A At 0°–5° C., treat the product of Preparation 2 (2.0 g) in CH$_2$Cl$_2$ (30 mL), with Proton Sponge ® (1.5 g) and the product of Preparation 5 (1.77 g) in CH$_2$Cl$_2$ (25 mL). Warm to room temperature (as ice melts) and stir overnight. Dilute the mixture with Et$_2$O and filter. Extract the Et$_2$O solution with water (3 times), dry over MgSO$_4$ and concentrate in vacuo to a residue. Chromatograph the residue on silica gel (40μ, 400 mL) using 1:99 MeOH:CH$_2$Cl$_2$ as eluant to give the product

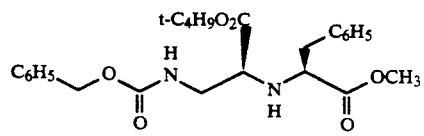

$[\alpha]^{20}$D = −1.8° (MeOH)

Using appropriate starting materials and substantially the same procedure, the following compounds can also be prepared:

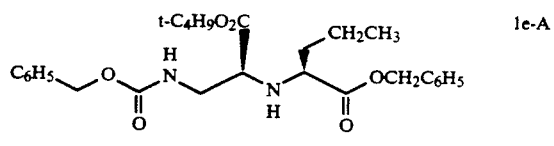

1e-A $[\alpha]^{22.5}$D = −13.4° (MeOH)

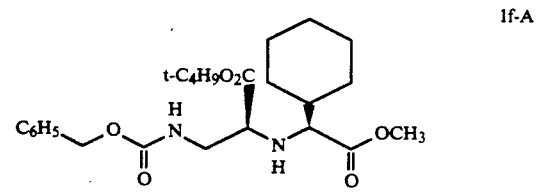

1f-A $[\alpha]^{22.5}$D = −1.1° (MeOH)

Step B: At 0°–5° C., treat the product of Step A (12.3 g) in MeOH (150 mL) with 4 portions of 1N NaOH (32 mL) over 5 min. Warm to room temperature and stir for 2.25 hr. Add acetic acid and concentrate in vacuo. Add MeOH and concentrate in vacuo to a residue. Chromatograph the residue on silica gel (40μ, 800 mL) using CH$_2$Cl$_2$:MeOH:glacial AcOH 310:10:1 (2250 mL); 230:10:1 (2500 mL) to give the product

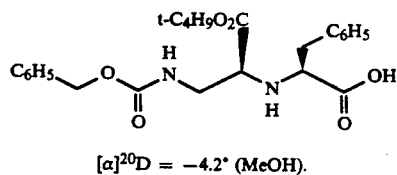

[α]²⁰D = −4.2° (MeOH).

Using appropriate starting materials and substantially the same procedure, the following compounds can also be prepared:

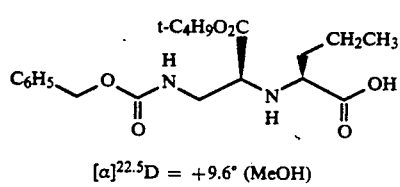

[α]²²·⁵D = +9.6° (MeOH)

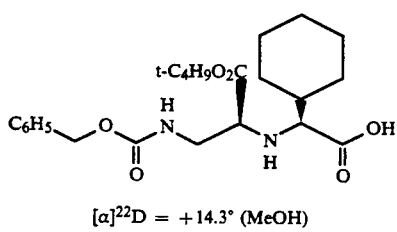

[α]²²D = +14.3° (MeOH)

Step C: Add EDCl (0.46 g) to the product of Step B (0.83 g), O-t-butyl-L-tyrosine t-butyl ester hydrochloride (0.66 g), HOBT (0.080 g) and triethylamine (0.63 mL) in DMF (5 mL) and stir the resulting mixture at room temperature overnight. Dilute with Et₂O (150 mL) and wash with water (2×50 mL), 1N HCl (2×25 mL), water (50 mL), 1N NaHCO₃ (25 mL), and water (50 mL). Concentrate the dried (MgSO₄) Et₂O solution in vacuo to give residue A. Neutralise the HCl extract with 1N NaHCO₃ and extract with CH₂Cl₂. Concentrate the dried (MgSO₄) CH₂Cl₂ in vacuo to give residue B. Combine residues A and B and chromatograph on silica gel plates (10, 1000μ plates) using 2% MeOH in CH₂Cl₂ to give the product

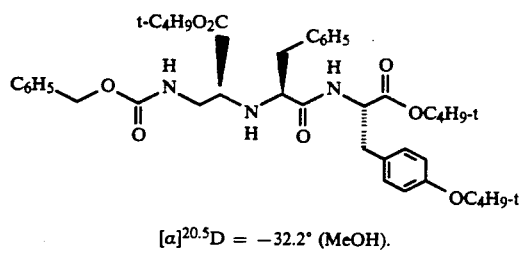

[α]²⁰·⁵D = −32.2° (MeOH).

Using appropriate starting materials, and substantially the same procedure, the following compounds can also be prepared:

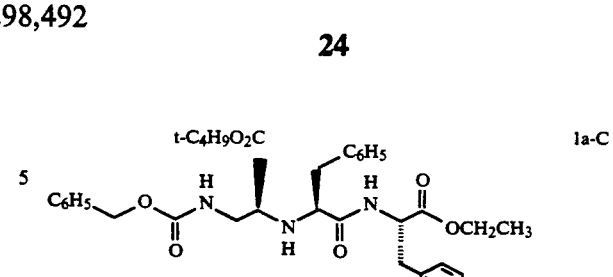

[α]²⁴·⁵D = −23.0° (MeOH)

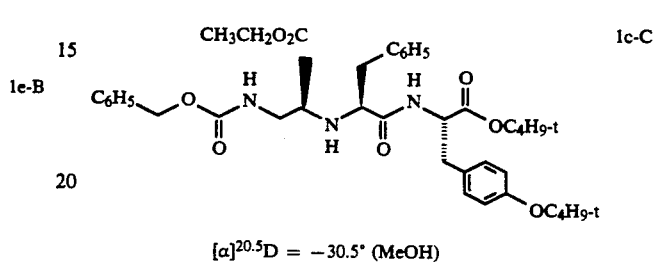

[α]²⁰·⁵D = −30.5° (MeOH)

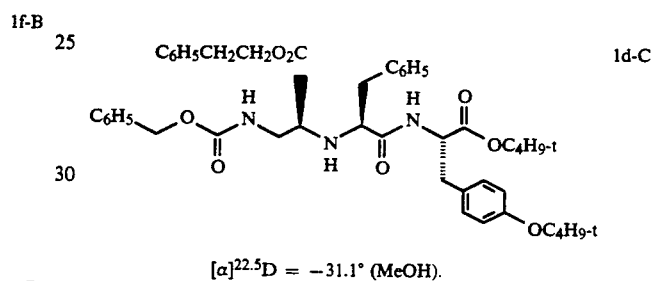

[α]²²·⁵D = −31.1° (MeOH).

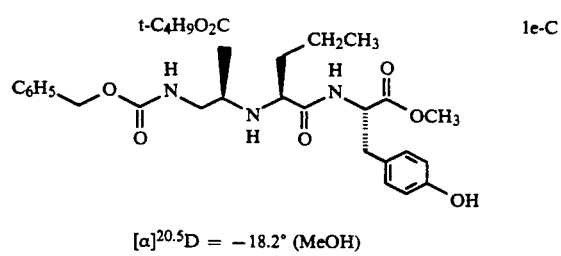

[α]²⁰·⁵D = −18.2° (MeOH)

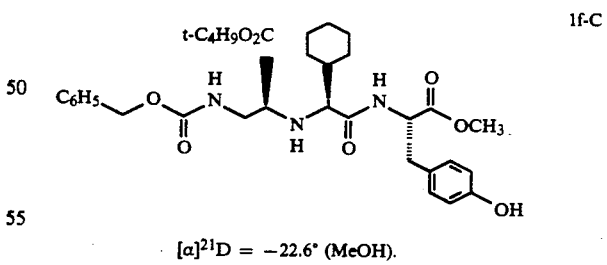

[α]²¹D = −22.6° (MeOH).

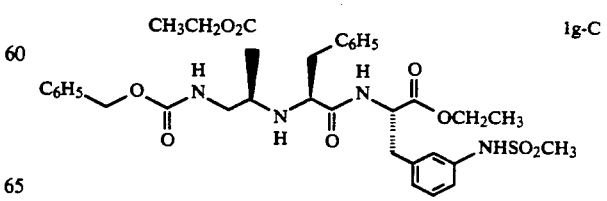

[α]²²D = −28.2° (MeOH)

-continued

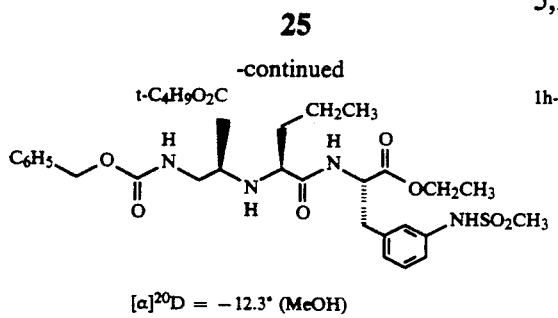

[α]²⁰D = −12.3° (MeOH)

Step D: Hydrogenate the Product of Step C (0.5 g) with 10% Pd/C (0.15 g) in MeOH (25 mL) at 50 psi for 3 hr. Filter and concentrate the filtrate in vacuo to give the product

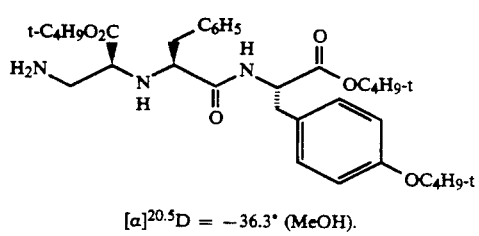

[α]²⁰·⁵D = −36.3° (MeOH).

Using appropriate starting materials and substantially the same procedure, the following compounds can also be prepared:

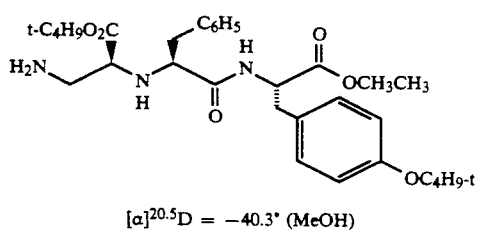

1a-D

[α]²⁰·⁵D = −40.3° (MeOH)

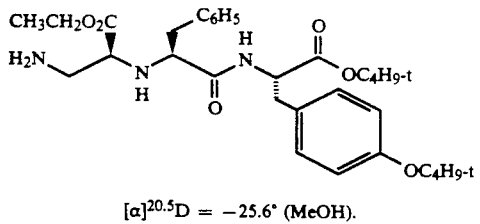

1c-D

[α]²⁰·⁵D = −25.6° (MeOH).

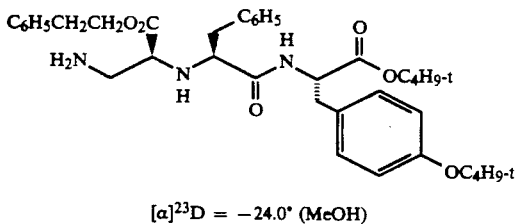

1d-D

[α]²³D = −24.0° (MeOH)

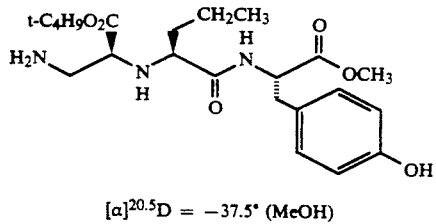

1e-D

[α]²⁰·⁵D = −37.5° (MeOH)

-continued

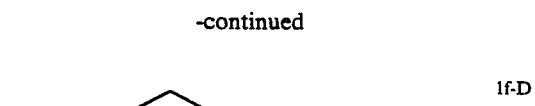

1f-D

[α]²⁰·⁵D = −43.0° (MeOH)

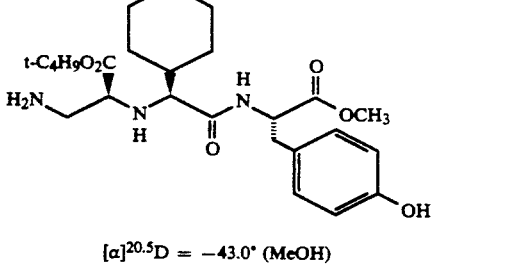

1g-D

[α]²³D = −32.0° (MeOH)

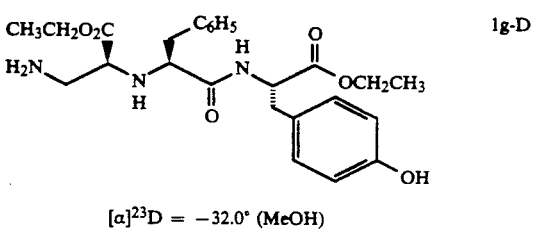

1h-D

[α]²⁰D = −12.0° (MeOH).

Step E: Add EDCl (0.11 g) to N⁶-benzyloxycarbonyl-N²-methanesulfonyl-L-lysine (0.19 g), the product of Step D (0.255 g), HOBT (0.014 g), and triethylamine (0.085 mL) in DMF (1 mL) and stir overnight at room temperature. Concentrate the reaction mixture in vacuo and dilute with Et₂O (50 mL). Wash the Et₂O solution with 1N NaHCO₃ (75 mL, then 50 mL), water (2×50 mL), and brine (2×25 mL). Concentrate the dried (MgSO₄) Et₂O solution in vacuo to a residue. Chromatograph the residue on silica gel (40μ, 500 mL) using MeOH:CH₂Cl₂ 1:99 (2000 mL) and then 1.5:98.5 to give the product

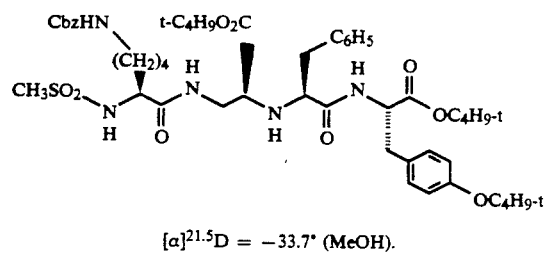

[α]²¹·⁵D = −33.7° (MeOH).

Using appropriate starting materials and substantially the same procedure, the following compounds can also be prepared:

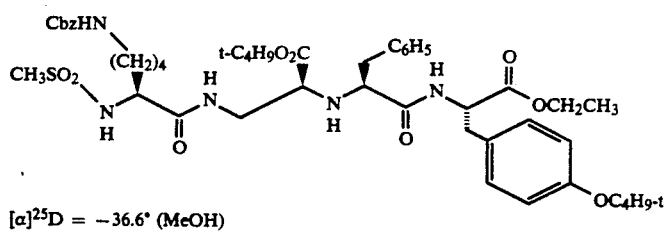

1a-E $[\alpha]^{25}D = -36.6°$ (MeOH)

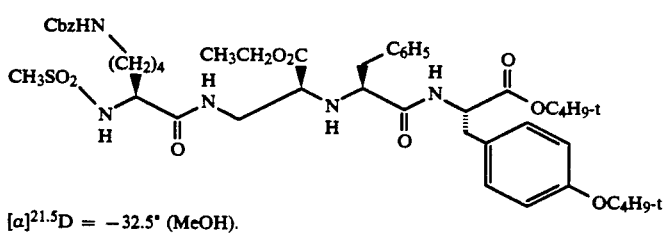

1c-E $[\alpha]^{21.5}D = -32.5°$ (MeOH).

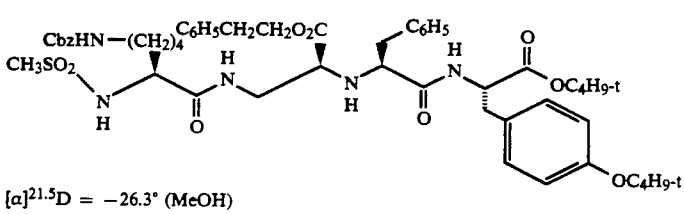

1d-E $[\alpha]^{21.5}D = -26.3°$ (MeOH)

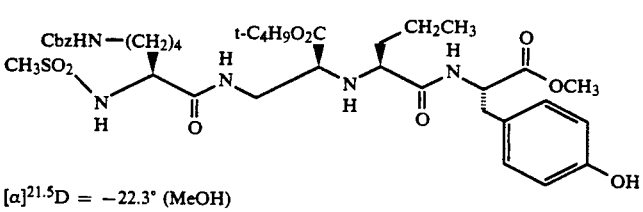

1e-E $[\alpha]^{21.5}D = -22.3°$ (MeOH)

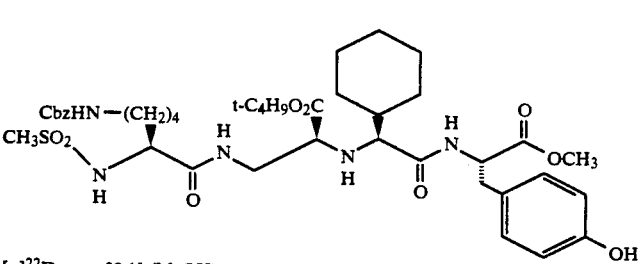

1f-E $[\alpha]^{22}D = -32.1°$ (MeOH)

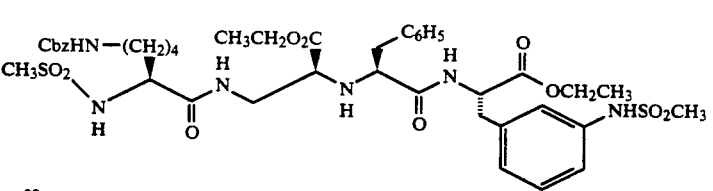

1g-E $[\alpha]^{20}D = -28.9°$ (MeOH)

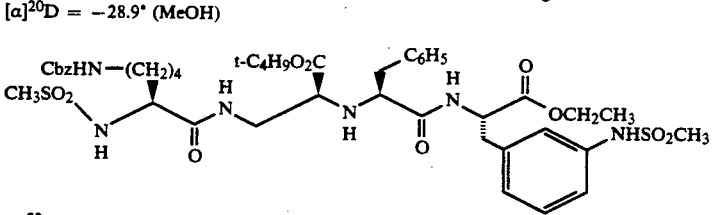

1h-E $[\alpha]^{22}D = -22.8°$ (MeOH)

Step F: Cool the product of Step E (2.0 g) in $CH_2Cl_2$ (10 mL) to 0°–5° C., add TFA (10 mL), stir for 30 min, then warm to room temperature and stir for 2 hr. Concentrate the reaction mixture in vacuo to a residue. Dissolve the residue in $Et_2O$ (115 mL), add 15% NaOH, and extract with $Et_2O$. Acidify the aqueous solution with glacial AcOH to pH 5 and extract with EtOAc (3×50 mL). Concentrate the dried (MgSO₄) EtOAc solution in vacuo to give the product

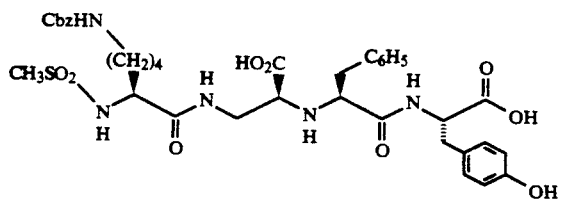

$[\alpha]^{22.5}D = -17.4°$ (MeOH).

Using appropriate starting materials and substantially the same procedure (leaving out the NaOH treatment), the following compounds can also be prepared:

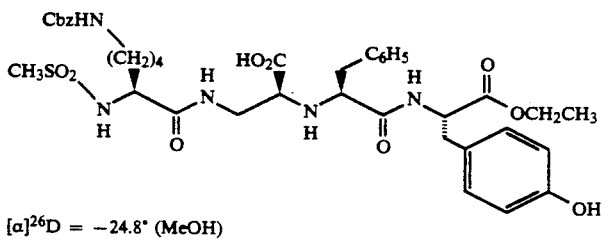

1a-F $[\alpha]^{26}D = -24.8°$ (MeOH)

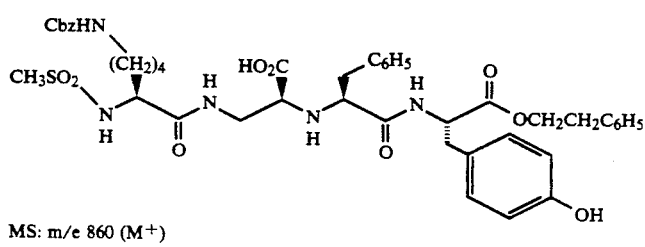

1b-F

MS: m/e 860 (M⁺)

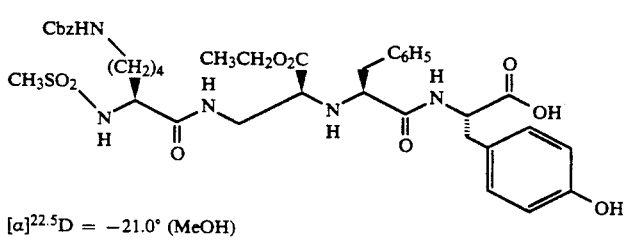

1c-F $[\alpha]^{22.5}D = -21.0°$ (MeOH)

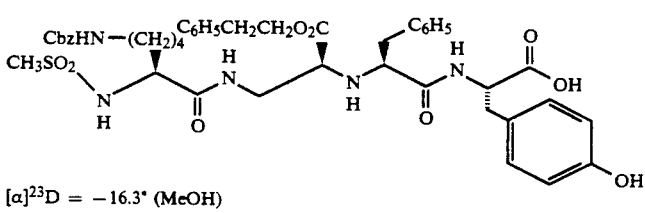

1d-F $[\alpha]^{23}D = -16.3°$ (MeOH)

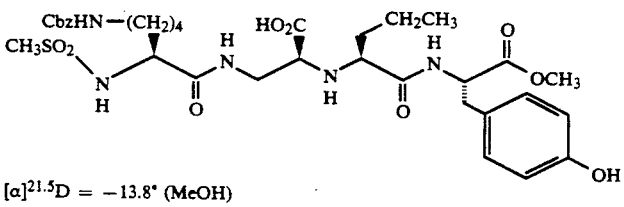

1e-F $[\alpha]^{21.5}D = -13.8°$ (MeOH)

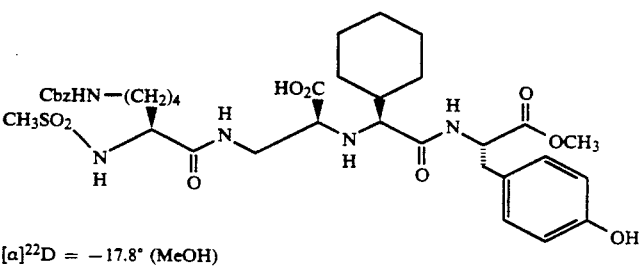

1f-F $[\alpha]^{22}D = -17.8°$ (MeOH)

-continued

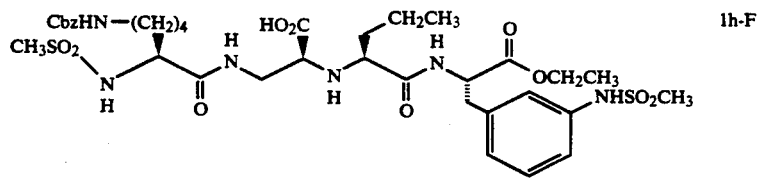

1h-F $[\alpha]^{22.5}D = -9.5°$ (MeOH)

Step G: Hydrogenate the product of step F (0.5 g) in MeOH (30 mL) with 10% Pd/C (0.5 g) at 50 psi for 2 hr. Filter through celite and concentrate the filtrate in vacuo to give the title compound, m.p. 150° C. (decomp), $[\alpha]^{22.5}D = -20.0°$ (MeOH).

Using appropriate starting materials, the following compounds can be prepared using substantially the same procedure.

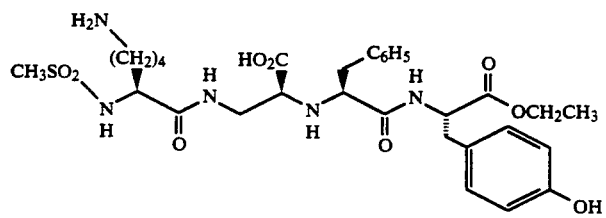

1a $[\alpha]^{22.5}D = -19.6°$ (MeOH)

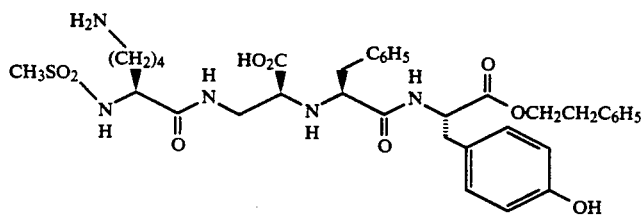

1b $[\alpha]^{23}D = -13.9°$ (MeOH)

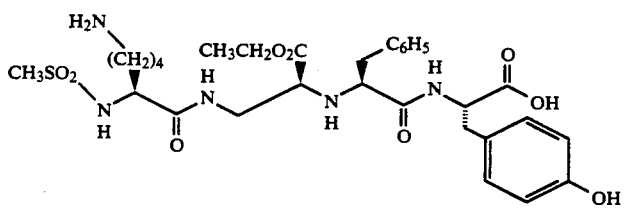

1c $[\alpha]^{23}D = -21.1°$ (MeOH)

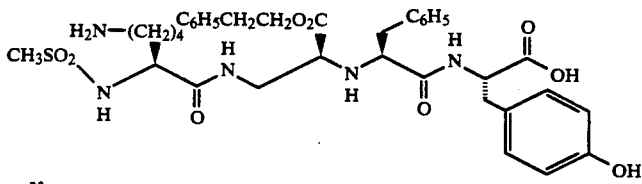

1d $[\alpha]^{23}D = -18.3°$ (MeOH)

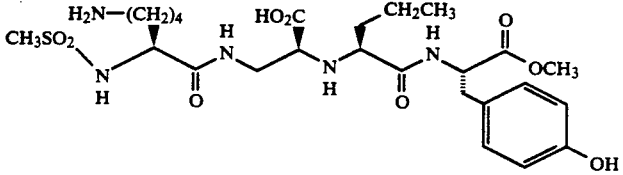

1e $[\alpha]^{21.5}D = -15.3°$ (MeOH).

-continued

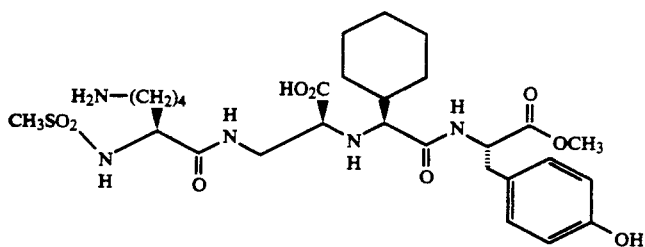

MS: m/e 628 (M+)

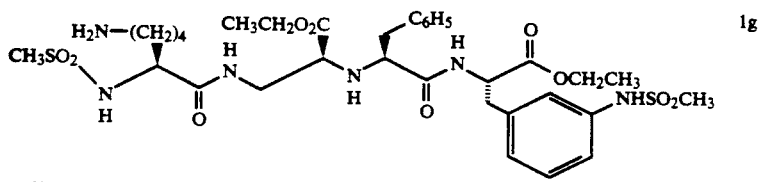

$[\alpha]^{22}D = -31.1°$ (MeOH)

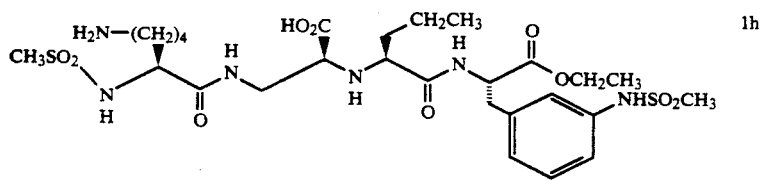

$[\alpha]^{22.5}D = -9.5°$ (MeOH)

EXAMPLE 2

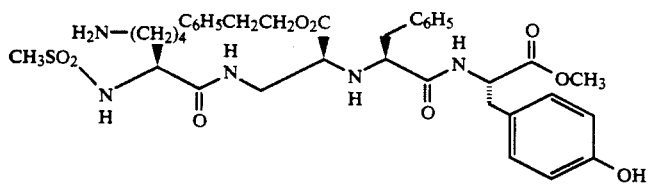

Step A: Add EDCl (1.50 g) to the product P10a of Preparation 10 (2.60 g), L-tyrosine methyl ester (1.80 g), HOBT (0.27 g) and triethylamine (1.80 mL) in DMF (10 mL) and treat the reaction mixture as described in Example 1, Step C to give a residue. Chromatograph the residue on silica gel (40μ, 300 mL) using 1% MeOH in CH₂Cl₂ to give the product.

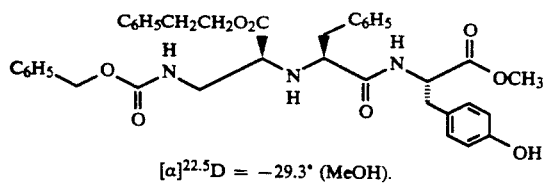

$[\alpha]^{22.5}D = -29.3°$ (MeOH).

Step B: Hydrogenate the product of Step A (2.1 g) with 10% Pd/C (0.50 g) in MeOH (60 mL) at 50 psi for 3 hr. Filter and concentrate the filtrate in vacuo to give a mixture of products

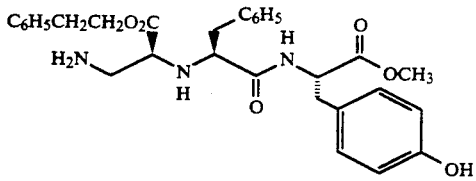

and

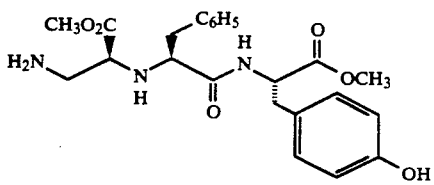

Step C Add EDCl (0.76 g) to the product mixture from Step B (2.00 g), N⁶-benzyloxycarbonyl-N²-methanesulfonyl-L-lysine (1.42 g), HOBT (0.14 g), and triethylamine (0.76 mL) in DMF (10 mL) and treat as described in Example 1, Step E to give a residue. Chromatograph the residue on silica gel (40μ, 350 mL) using MeOH:CH₂Cl₂ 1:99 to give Fractions A and B. Chromatograph Fraction A on silica gel plates (10, 1000μ) using CH₂Cl₂:MeOH:NH₄OH 110:10:1 to give product 2-C-I

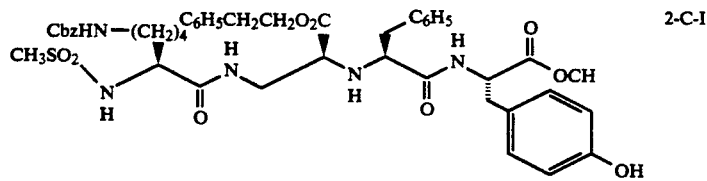

2-C-I $[\alpha]^{22.5}D = -23.8°$ (MeOH).

Chromatograph Fraction B on silica gel plates (10, 1000μ,) using CH$_2$Cl$_2$:MeOH:NH$_4$OH 110:10:1 to give product 2-C-II

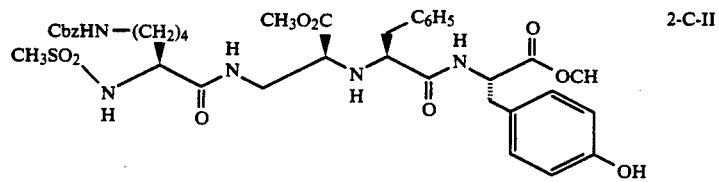

2-C-II $[\alpha]^{20.5}D = -26.6°$ (MeOH).

Step D Hydrogenate compound 2-C-I from step C (0.45 g) in DMF (18 mL) with 10% Pd/C (0.41 g) at 50 psi for 5.5 hr. Filter through celite and concentrate the filtrate in vacuo to give a residue. Chromatograph the residue on silica gel plates (6, 1000μ) using CH$_2$Cl$_2$:MeOH:NH$_4$OH 70:10:1 as eluant to give the title compound, $[\alpha]^{21}{}_D = -24.3°$ (MeOH).

Using MeOH as the solvent and following substantially the same procedure, hydrogenate compound 2-C-II from Step C to give compound

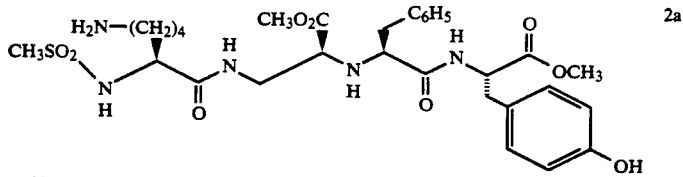

2a $[\alpha]^{21}D = -29.6°$ (MeOH).

EXAMPLE 3

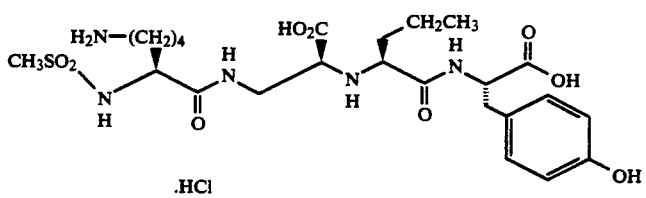

.HCl

Stir the compound of Example 1e (0.70 g) in acetone (1 mL) with 1N NaOH (2 mL) for 1.5 hr. Acidify with 2N HCl (4 mL) and allow to concentrate under nitrogen to a residue. Triturate the residue with Et$_2$O and filter. Stir the residue with cold MeOH (2×2 mL) then hot MeOH (4 mL) and filter. Concentrate the MeOH solution in vacuo to give the title compound, $[\alpha]^{22}{}_D = -6.9°$ (MeOH).

Using appropriate starting materials and substantially the same procedure, the following compounds were also prepared:

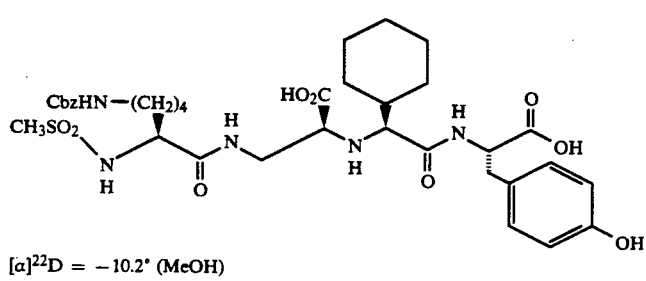

3a $[\alpha]^{22}D = -10.2°$ (MeOH)

-continued

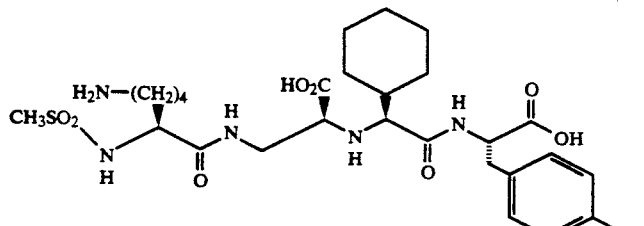

[α]²²D = −4.8° (MeOH)

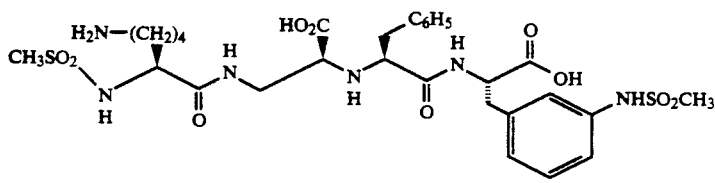

[α]²²·⁵D = −19.2° (MeOH)

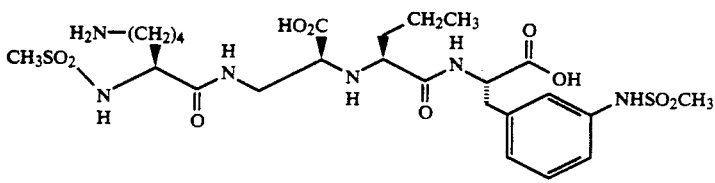

[α]²²D = −3.6° (MeOH)

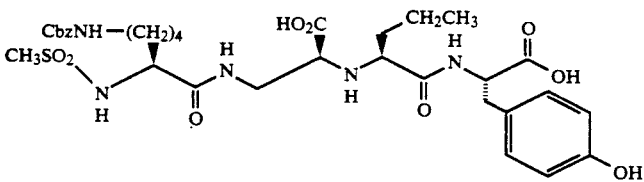

[α]²²·⁵D = −6.2° (MeOH)

50 psi for 3 hr. Filter and concentrate the filtrate in vacuo to give the product

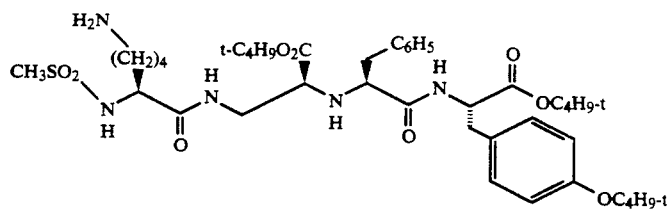

Step B: Heat the product of Step A (1.3 g), N,N-diethylcarbodiimide (0.46 g), diisopropylethylamine (0.21 g), and p-TSA (0.25 g) in dioxane (30 mL) under reflux for 6 hr. Concentrate the mixture in vacuo to a residue and dissolve the residue in CH₂Cl₂ (100 mL). Wash the CH₂Cl₂ solution with 1% NaOH/brine (3×50 mL); brine/water; and brine. Concentrate the dried (MgSO₄) CH₂Cl₂ in vacuo to give a residue. Chromatograph this residue on silica gel plates (11, 1000μ) using CH₂Cl₂:MeOH:AcOH 70:10:1 as eluant to give the product

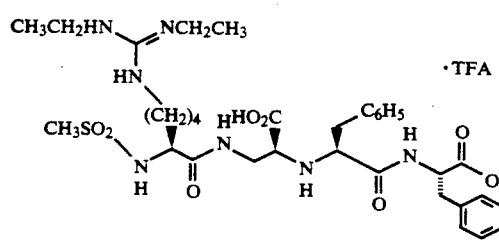

Step A: Hydrogenate the product of Example 1, Step E (3.0 g) in MeOH (35 mL) with 10% Pd/C (0.83 g) at

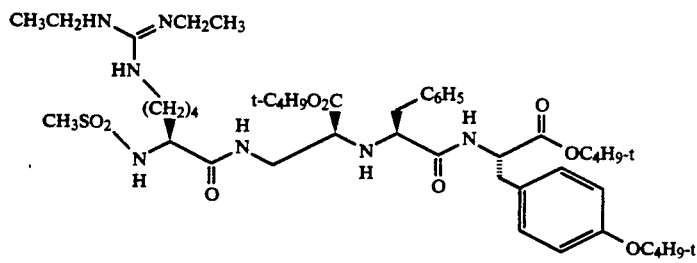

$[\alpha]_D^{22.5} = -19.6°$ (MeOH).

Step C: Under a dry nitrogen atmosphere, treat the product of Step B (0.28 g) with TFA (3 mL) and stir overnight. Concentrate the reaction under nitrogen, twice add CH₂Cl₂ then concentrate in vacuo to a residue. Triturate the residue with Et₂O to give the title compound, $[\alpha]^{23}{}_D = -14.5°$ (MeOH).

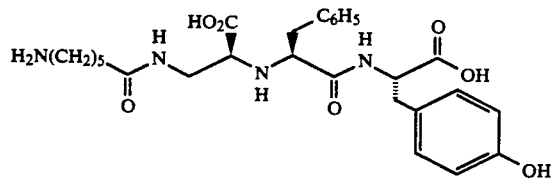

Step A: Add EDCl (1.00 g) to 6-benzyloxycarbonylaminohexanoic acid (1.20 g), the product of Example 1, Step D (2.15 g), and HOBT (0.067 g) in DMF (7 mL), and treat as described in Example 1, Step E to give a residue. Chromatograph the residue on silica gel (40 μ, 300 mL) using MeOH:CH₂Cl₂ 0.75:99.25; 1:99 to give the product give a residue. Triturate the residue with Et₂O and filter to give the product

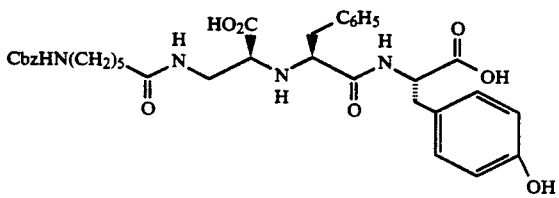

m.p. 98–102° C., $[\alpha]_D^{22.5} = -9.9°$ (MeOH).

Step C: Hydrogenate the product of Step B (1.00 g) in MeOH (30 mL), with 10% Pd/C (0.37 g) at 50 psi for 2 hr. Filter and concentrate the filtrate in vacuo to give the title compound, $[\alpha]^{23}{}_D = -7.2°$ (MeOH).

EXAMPLE 6

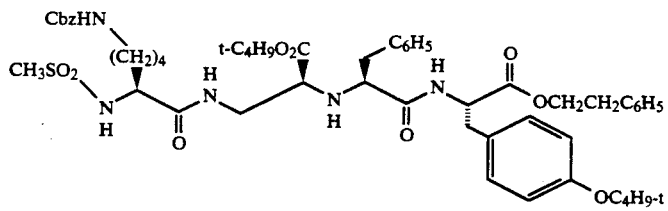

Step A: Treat product 1a-E of Example 1, Step E (3.3 g) in acetone (7.5 mL) portionwise with 1N NaOH (7.5 mL) over 1 min., and stir for 30 min. Add 10% citric acid to pH 5–6 and extract with EtOAc (3×25 mL). Extract the EtOAc solution with brine. Concentrate the dried (MgSO₄) EtOAc solution in vacuo to give the product

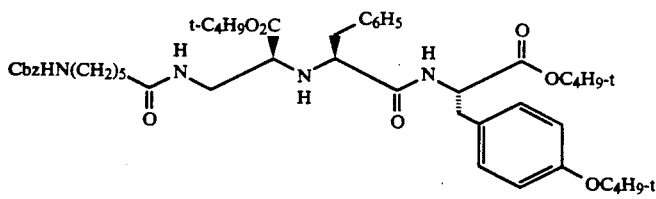

$[\alpha]_D^{24.5} = -19.0°$ (MeOH).

Step B: Cool the product of Step A (2.20 g) in CH₂Cl₂ (15 mL) to 0°–5° C., add TFA (15 mL), and stir overnight. Concentrate the reaction mixture in vacuo to

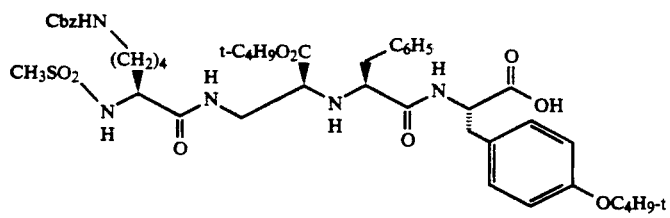

$[\alpha]_D^{26} = -30.0°$ (MeOH).

Step B: Stir the product of Step A (1.5 g) in DMF (5 mL) with cesium carbonate (0.56 g) and phenethyl bromide (0.75 mL) at room temperature overnight. Add glacial AcOH and concentrate in vacuo to give a residue. Dissolve the residue in EtOAc (100 mL), extract with water (2×35 mL) and then brine. Concentrate the dried (MgSO₄) EtOAc in vacuo to give a residue. Chromatograph this residue on silica gel (40 μ, 300 mL) using MeOH:CH₂Cl₂ 99:1 (2000 mL), then 98.75:1.25 to give the title compound, $[\alpha]^{26}_D = -32.8°$ (MeOH).

EXAMPLE 7

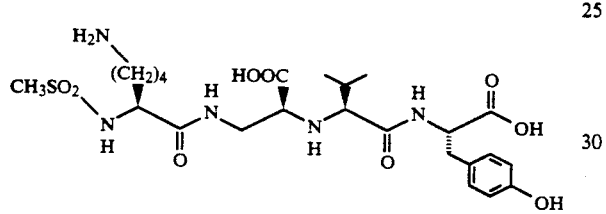

Step A: Treat 10.0 g of the product of Preparation 11 in 100 mL of CH₂Cl₂, at 0° to 5° C., with 8.0 g of Proton Sponge ® and a solution of 17.0 g of valine t-butyl ester in 100 mL of CH₂Cl₂. Warm the mixture to room temperature and stir overnight. Dilute the mixture with ether, filter, then wash the filtrate with water. Concentrate to a residue, which is chromatographed on silica gel (1:3 ethyl acetate/hexane) to give the product

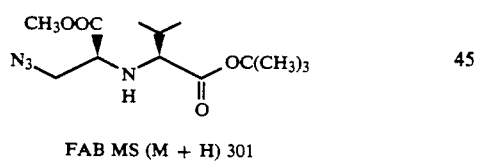

FAB MS (M + H) 301

The following compounds can be prepared using substantially the same procedures:

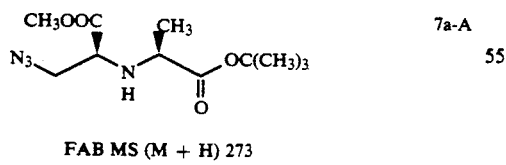
FAB MS (M + H) 273

7a-A

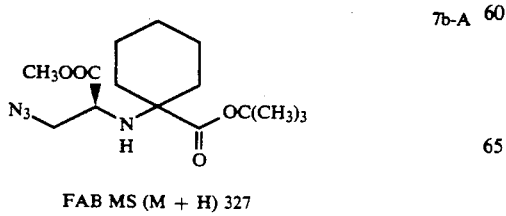
FAB MS (M + H) 327

7b-A

-continued

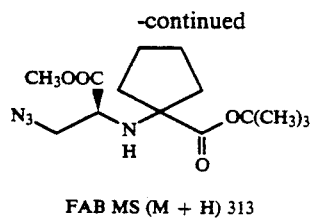
FAB MS (M + H) 313

7c-A

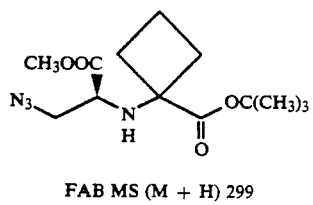
FAB MS (M + H) 299

7d-A

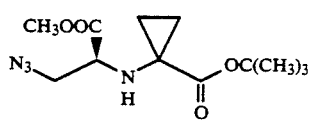
FAB MS (M + H) 285

7e-A

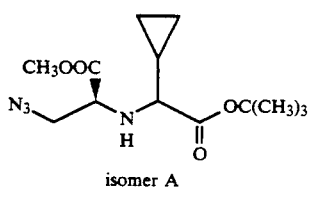
isomer A
FAB MS (M + H) 299

7f-A

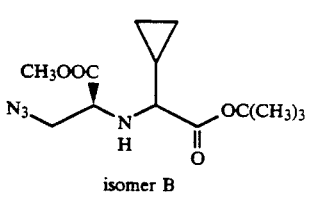
isomer B
FAB MS (M + H) 299

7g-A

Step B: Dissolve 5.0 g of the product of step A in 20 mL of CH₂Cl₂ and treat with 20 mL of trifluoroacetic acid (TFA) at room temperature overnight. Concentrate to a residue, add diethyl ether and concentrate again several times to give the product:

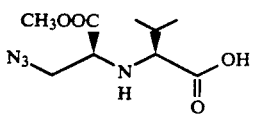

¹H NMR (200 MHz, CDCl₃) 4.12 (dd, J=5.0, 7.0 Hz, 1H); 4.22–4.04 (2dd, J=12.5, 5.0 Hz and J=12.5, 7.0 Hz, 2H); 3.90 (s, 3H); 2.50 (m, 1H); 0.95–0.98 (2d, 5.6 Hz, 6H).

Substantially the same procedure is used to prepare the following compounds:

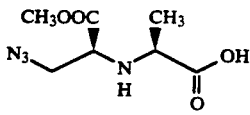

FAB MS (M + H) 217

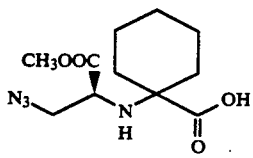

FAB MS (M + H) 271

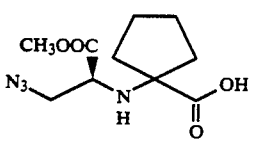

FAB MS (M + H) 257

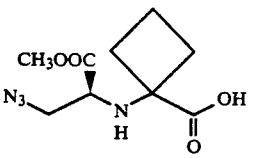

FAB MS (M + H) 243

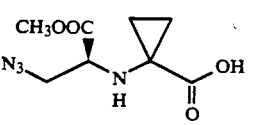

FAB MS (M + H) 229

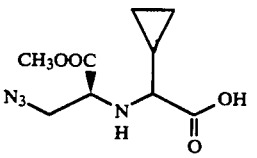

isomer A

FAB MS (M + H) 243

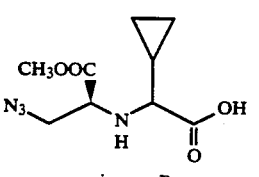

isomer B

FAB MS (M + H) 243

Step C: Add 2.85 g of EDCl to a mixture of 3.30 g of the product of step B, 4.45 g of O-t-butyl-L-tyrosine-t-butyl ester hydrochloride, 1.82 g of HOBT, 5 mL of triethylamine and 15 mL of DMF, and stir overnight at room temperature. Dilute the mixture with 500 mL of diethyl ether, wash with water (2×100 mL), dry over MgSO₄, filter, and concentrate to a residue. Chromatograph the residue on silica gel (30:70 ethyl acetate/hexane) to give the product:

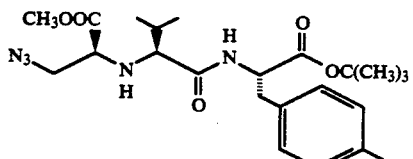

¹H NMR (200 MHz, CDCl₃) 7.50 (1H); 6.90–7.10 (2d, J=8 Hz, 4H); 4.72 (dd, J=5.0, 7.0 Hz, 1H); 3.74 (s, 3H); 3.58 (d, J=4.0 Hz, 2H); 3.42 (t, J=4.0 Hz, 1H); 3.00–3.05 (2×dd, J=13.8, 7.09 Hz and J=13.8, 5.0 Hz, 2H); 2.94 (d, J=4.5 Hz, 1H); 2.0 (m, 1H); 1.32–1.42 (2s, 18H); 0.84–0.92 (2d, 5.5 Hz, 6H).

Using substantially the same procedures, the following compounds can be prepared:

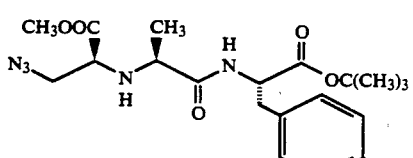

¹H NMR(200 MHz, CDCl₃) 7.6(br.d, 1H); 6.92–7.1(2 br.d, J=8.5Hz, 4H); 4.68(br.q, J=7.0 Hz, 1H); 3.75(s, 3H); 3.55–3.60(2 dd, J=15.0, 6.00 Hz and J=15.0, 6.5Hz, 2H); 3.37(dd, J=6.00, 6.50 Hz, 1H); 3.10(m, 1H); 3.00–3.05(2 dd, J=14.5, 7.0 Hz and J=14.5, 7.0 Hz and J=14.5, 6.5 Hz, 2H); 1.32–1.45(2s, 18H); 1.28(d, J=7.0Hz, 3H).

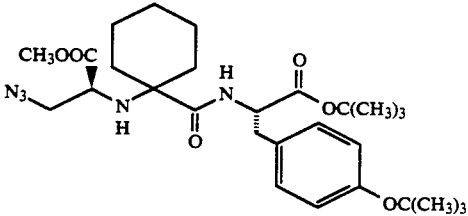

FAB MS (M + H) 546

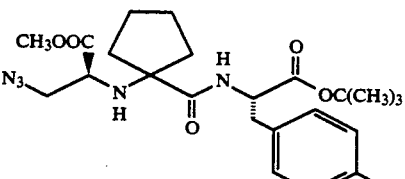

FAB MS (M + H) 532

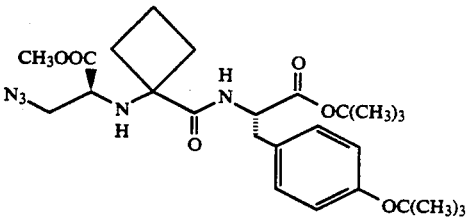

45
-continued

FAB MS (M + H) 518

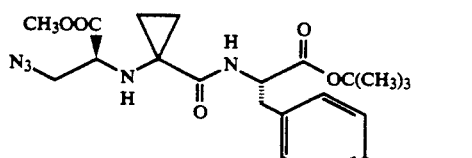

FAB MS (M + H) 504

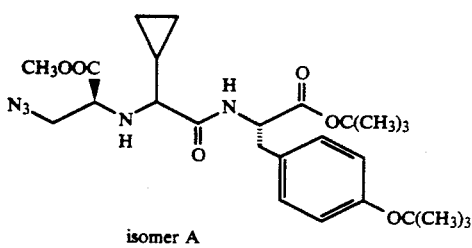

isomer A

FAB MS (M + H) 518

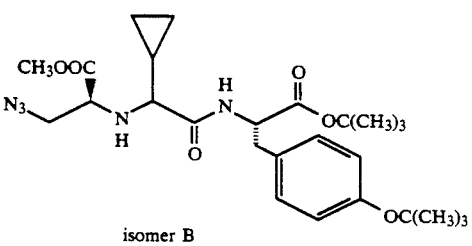

isomer B

46
-continued

FAB MS (M + H) 518

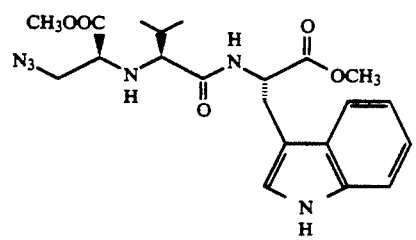   7e-C

7f-C

FAB MS (M + H) 445   7h-C

Step D: The product of step C (1.0 g) is combined with 0.50 g of 10% Pd on carbon and 50 mL of ethanol and hydrogenated at 60 psi for 4 h. Filter and concentrate the filtrate to a residue. Dissolve the residue in 2 mL of DMF, then add EDCl (0.45 g), $N^6$-benzyloxycarbonyl-$N^2$-methane-sulfonyl-L-lysine (0.75 g), HOBT (0.15 g) and triethylamine, and stir the mixture overnight at room temperature. Dilute the mixture with 20 mL of diethyl ether, wash with water (2×50 mL), dry over MgSO4, filter and concentrate to a residue. Chromatograph the residue on silica gel to give the product:

7g-C

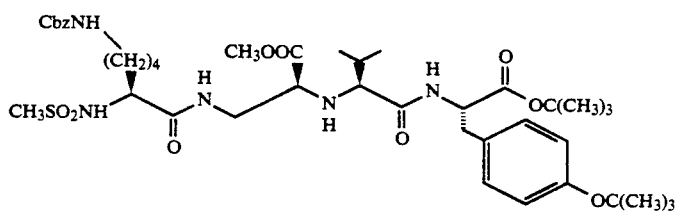

Cl MS (M + H) 834

Using a similar procedure, the following compounds can be prepared:

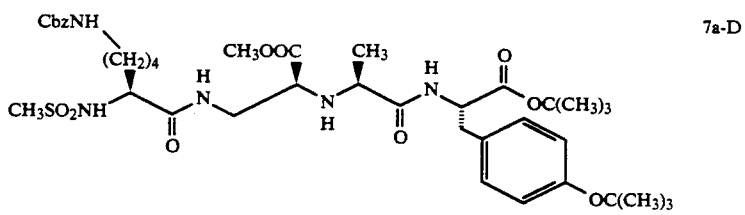   7a-D

FAB MS (M + H) 806

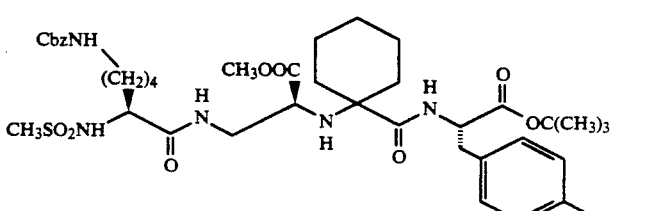   7b-D

FAB MS (M + H) 860

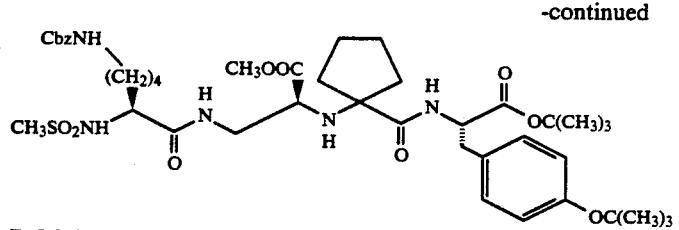

FAB MS (M + H) 846                                                              7c-D

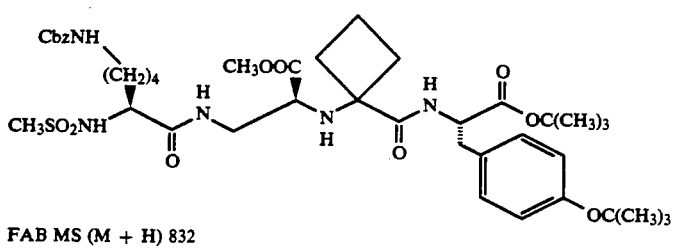

FAB MS (M + H) 832                                                              7d-D

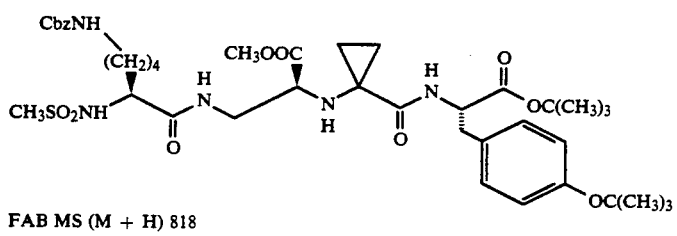

FAB MS (M + H) 818                                                              7e-D

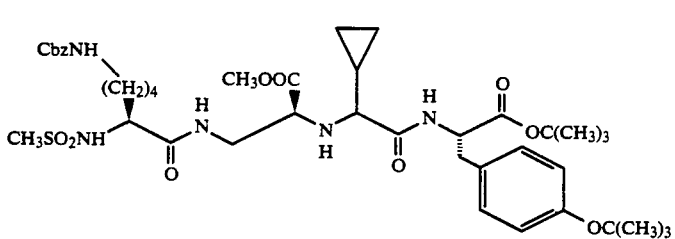

isomer A
FAB MS (M + H) 832                                                              7f-D

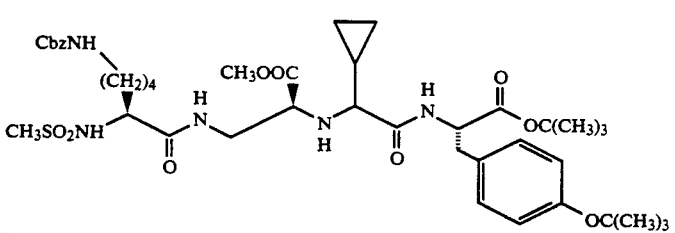

isomer B
FAB MS (M + H) 832                                                              7g-D

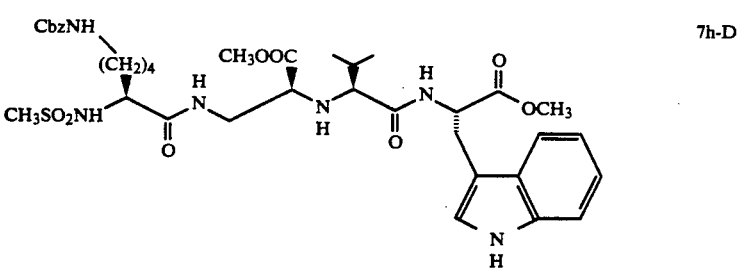

FAB MS (M + H) 759                                                              7h-D

Step E: Combine a solution of the product of step D (1.0 g) in methanol with a solution of LiOH (0.5 g) in water and stir the mixture at 0° to 25° C. for 2 h. Add 3N HCl to bring the mixture to pH=7 and remove the methanol under vacuum. Adjust the pH to 3 with additional acid and extract with 3×100 mL of ethyl acetate. Dry the extracts over MgSO$_4$ and concentrate to give the product:

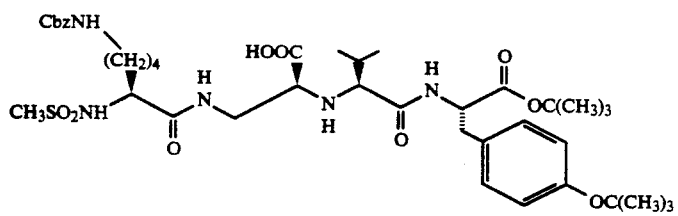

Cl MS (M+) 820

Using substantially the same procedure, the following compound can be prepared from compound 7j, of step G:

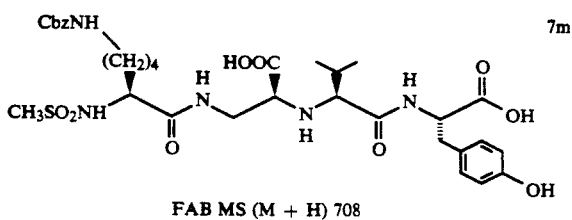

7m

FAB MS (M + H) 708

Step F: Combine 0.5 g of the product of step E, 0.20 g of 10% Pd on carbon and 30 mL of ethanol, and hydrogenate at 60 psi for 4 h. Filter and concentrate the filtrate to give the product:

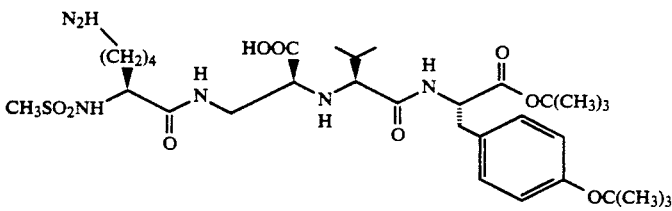

Cl MS (M + H) 686

Using substantially the same procedure, the following compound can be from compound 7j, of step G:

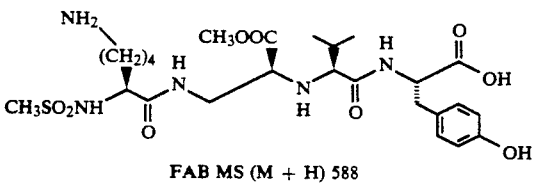

7k

FAB MS (M + H) 588

Step G: Cool a solution of 0.2 g of the product of step F in 2 mL of CH₂Cl₂ to 0° C., add 2 mL of TFA and stir for ½ h. Warm the mixture to room temperature and stir overnight. Concentrate to a residue and wash the residue with several portions of diethyl ether. Evaporate the residual ether under vacuum to give the title compound, Cl MS (M+H) 574.

Using substantially the same procedure, the following compounds can be prepared: from compound 7-D, of step D:

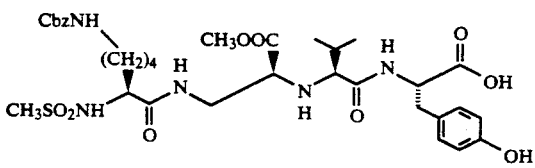

7j

-continued
FAB MS (M + H) 722

Using substantially the same procedure as described in steps E, F and G, compound 7a-D, of step D, can be converted to:

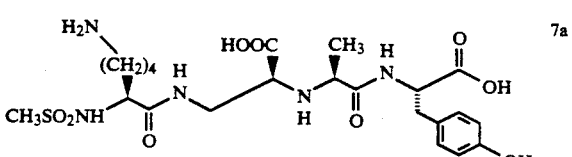

7a

FAB MS (M + Na) 568, (M + H) 546

EXAMPLE 8

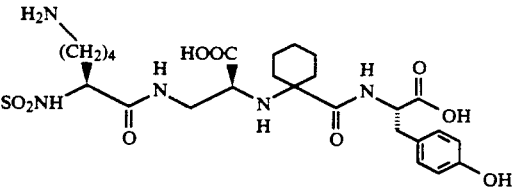

Step A: A solution of 0.5 g of compound 7b-D, from Example 7, step D, in 5 mL of CH₂Cl₂ is cooled to 0° C. Add 5 mL of TFA and stir at 0° C. for ½ h., then at room temperature overnight. Concentrate to a residue and wash the residue with several portions of ether. Remove the residual ether under vacuum to give the product:

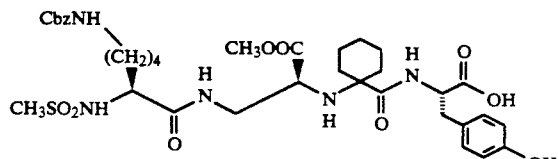

Step B: Hydrolyze the product of step A according to the procedure described in Example 7, step E to give the compound

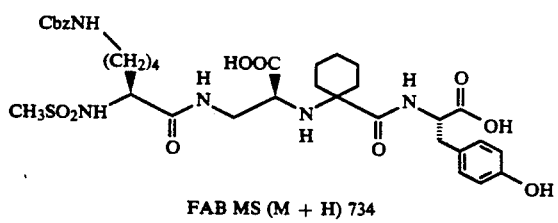

FAB MS (M + H) 734

Step C: Hydrogenate the product of step B according to the procedure described in Example 7, step F to give the title compound, FAB MS (M+1) 600.

The following compounds can be prepared by substantially the same procedures as in steps A, B and C:

from compound 7c-D, of Example 7, step D:

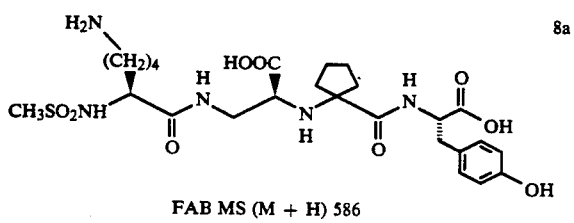

8a

FAB MS (M + H) 586 from compound 7d-D, of Example 7, step D:

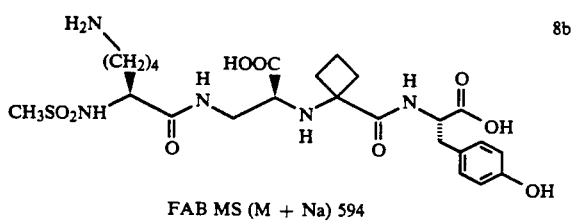

8b

FAB MS (M + Na) 594 from compound 7e-D, of Example 7, step D:

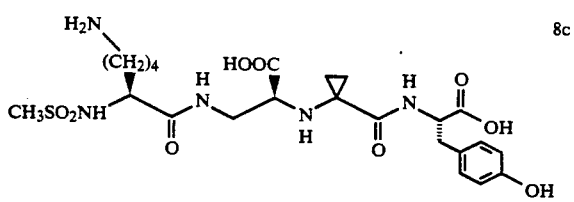

8c

-continued
FAB MS (M + H) 558, (M + Na) 580 from compound 7f-D, of Example 7, step D:

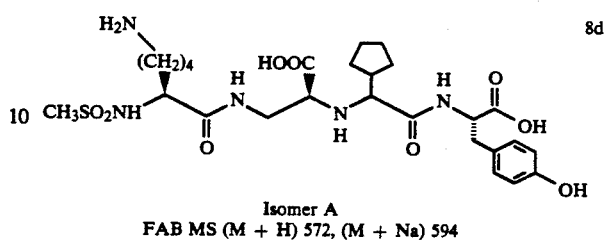

8d

Isomer A
FAB MS (M + H) 572, (M + Na) 594 from compound 7g-D, of Example 7, step D:

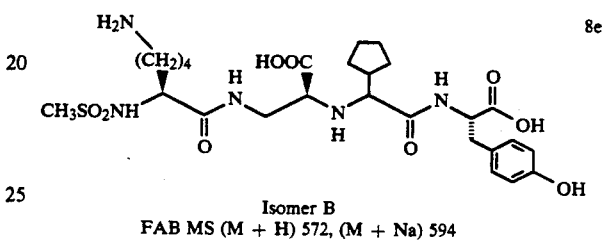

8e

Isomer B
FAB MS (M + H) 572, (M + Na) 594 from compound 7h-D, of Example 7, step D:

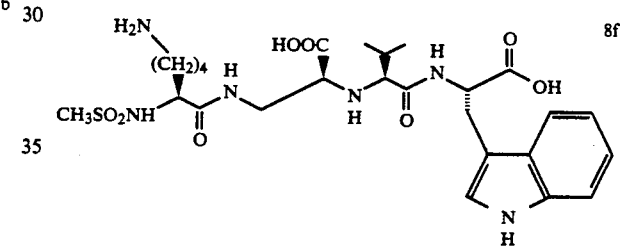

8f

FAB MS (M + H) 597

Using the methods described above, the following activity data were obtained for compounds of the formulae shown in the following tables. Changes in BP are expressed as mm Hg (dose) and A1 Challenge data are expressed as % inhibition (dose).

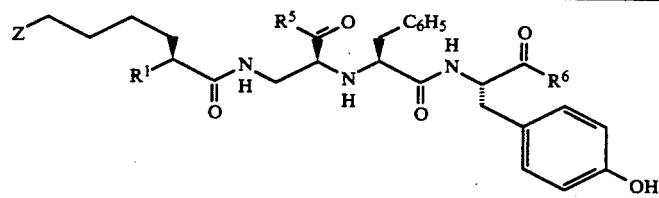

| $R^1$ | $R^5$ | $R^6$ | Z | IC$_{50}$, nM | | Change in BP | | | A1 Chall. |
|---|---|---|---|---|---|---|---|---|---|
| | | | | NEP | ACE | DOCA | FSHR | ANF Pot. | |
| CH$_3$SO$_2$NH | OH | OH | Cbz—NH— | 18 | 9 | 22 (10 po) | 7 (10 sc) 2 (30 sc) | 31 (30 sc) | 68% (30 sc) |
| CH$_3$SO$_2$NH | OH | OH | NH$_2$ | 35 | 50 | 53 (10 sc) 17 (10 po) 13 (30 po) | 40 (10 sc) | 16 (30 sc) | 96% (30 sc) |
| CH$_3$SO$_2$NH | OH | C$_2$H$_5$O | Cbz—NH— | 38 | 50 | 46 (10 sc) 10 (10 po) | 20 (10 sc) | 11 (30 sc) | 96% (10 sc) |
| CH$_3$SO$_2$NH | OH | C$_2$H$_5$O | NH$_2$ | 40 | 650 | 38 (10 po) | 26 (10 sc) | 1 (30 sc) | 89% (10 sc) |
| H | OH | OH | Cbz—NH— | 30 | 65 | 10 (10 po) | 1 (10 sc) | — | 64% (10 sc) |
| H | OH | OH | NH$_2$ | 16 | 60 | 13 (10 sc) | 9 (10 sc) | 17 (30 sc) | 100% |

-continued

| | | | | | | | | | | |
|---|---|---|---|---|---|---|---|---|---|---|
| CH₃SO₂NH | OH | C₆H₅—(CH₂)₂O | NH₂ | 68 | 175 | 0 (10 po) 36 (10 sc) 10 (10 po) | — | 9 (30 sc) | 93% (10 sc) | (10 sc) |
| CH₃SO₂NH | C₂H₅O | OH | Cbz—NH— | >300 | >1000 | 60 (10 sc) 13 (10 po) | 26 (10 sc) | 5 (3 sc) | 97% (10 sc) | |
| CH₃SO₂NH | C₂H₅O | OH | NH₂ | 300 | >1000 | 57 (10 sc) 19 (30 po) 15 (10 po) | 34 (10 sc) 1 (30 po) | 40 (30 sc) | 100% (10 sc) | |
| CH₃SO₂NH | C₆H₅—(CH₂)₂O | OH | Cbz—NH— | — | — | 2 (10 po) | 33 (10 sc) | — | — | |
| CH₃SO₂NH | C₆H₅—(CH₂)₂O | OH | NH₂ | — | — | 11 (10 po) | 39 (10 sc) | — | — | |
| CH₃SO₂NH | C₆H₅—(CH₂)₂O | CH₃O | NH₂ | — | — | 0 (10 po) | 35 (10 sc) 6 (30 po) | — | — | |
| CH₃SO₂NH | CH₃O | CH₃O | NH₂ | — | — | 26 (10 po) | 34 (10 sc) 9 (30 po) | — | — | |
| CH₃SO₂NH | C₆H₅—(CH₂)₂O | CH₃O | CBz—NH— | — | — | 31 (10 po) | 5 (10 sc) 2 (30 po) | — | — | |
| CH₃SO₂NH | OH | OH | NH—C₂H₅ \| C=NC₂H₅ \| NH | 95 | 8 | 5 (10 po) | — | — | — | |

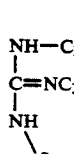

| $R^1$ | $R^2$ | $R^3$ | $R^5$ | $R^6$ | Z | IC₅₀, nM NEP | IC₅₀, nM ACE | Change in BP DOCA | Change in BP FSHR |
|---|---|---|---|---|---|---|---|---|---|
| CH₃SO₂NH | benzyl | H | C₂H₅O | C₂H₅O | NH₂ | — | — | 20 (10 po) | 0 (30 po) |
| CH₃SO₂NH | n-Pr | H | OH | C₂H₅O | Cbz—NH— | 70 | 400 | — | 33 (10 sc) 11 (30 po) |
| CH₃SO₂NH | n-Pr | H | OH | C₂H₅O | NH₂ | — | — | 12 (10 po) | 5 (30 po) |
| CH₃SO₂NH | n-Pr | H | OH | OH | NH₂ | 200 | 40 | 22 (10 po) | 9 (30 po) |
| CH₃SO₂NH | benzyl | H | OH | OH | NH₂ | 25 | 15 | 10 (10 po) | |

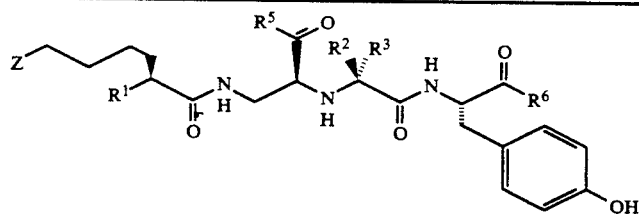

| $R^1$ | $R^2$ | $R^3$ | $R^5$ | $R^6$ | Z | IC₅₀, nM NEP | IC₅₀, nM ACE | Change in BP DOCA | Change in BP FSHR |
|---|---|---|---|---|---|---|---|---|---|
| CH₃SO₂NH | i-Pr | H | OH | OH | Cbz—NH— | 2 | 30 | 22 (10 po) | 37 (10 sc) |
| CH₃SO₂NH | i-Pr | H | OH | OH | NH₂ | 7 | 50 | 44 (10 po) 14 (1 po) | 69 (10 sc) 29 (100 po) 19 (30 po) 12 (10 po) |
| CH₃SO₂NH | i-Pr | H | CH₃O | OH | Cbz—NH— | 240 | >1000 | 48 (10 sc) | — |
| CH₃SO₂NH | i-Pr | H | CH₃O | OH | NH₂ | >300 | >1000 | 12 (10 po) | 44 (3 sc) |
| CH₃SO₂NH | n-Pr | H | OH | CH₃O | Cbz—NH— | 78 | 300 | 12 (10 po) | 5 (3 po) |
| CH₃SO₂NH | n-Pr | H | OH | CH₃O | NH₂ | 270 | — | 19 (10 po) | 38 (10 sc) 6 (30 po) |
| CH₃SO₂NH | n-Pr | H | OH | OH | NH₂ | 6 | 30 | 12 (10 po) | 28 (10 sc) 17 (30 po) |
| CH₃SO₂NH | n-Pr | H | OH | OH | Cbz—NH— | 2 | 15 | — | 0 (30 po) |
| CH₃SO₂NH | CH₃ | H | OH | OH | NH₂ | — | — | 22 (10 po) | 19 (10 po) |
| CH₃SO₂NH | —(CH₂)₂— | | OH | OH | NH₂ | >300 | 150 | 1 (10 po) | 26 (10 sc) 9 (30 po) |

-continued

| R¹ | (CH₂)ₘ | R⁵ | R² | R³ | R⁴ | NEP | ACE | DOCA | FSHR |
|---|---|---|---|---|---|---|---|---|---|
| CH₃SO₂NH | —(CH₂)₄— | | OH | OH | NH₂ | 35 | 45 | 20 (10 po) | 32 (10 sc) |
| CH₃SO₂NH | —(CH₂)₅— | | OH | OH | NH₂ | 190 | — | 10 (10 po) | 11 (10 sc) |
| | | | | | | | | | 1 (30 po) |
| CH₃SO₂NH | —(CH₂)₃— | | OH | OH | NH₂ | 42 | — | 15 (10 po) | — |
| CH₃SO₂NH | cyclohexyl | H | OH | CH₃O | Cbz—NH— | — | — | 12 (10 po) | 0 (10 sc) |
| CH₃SO₂NH | cyclohexyl | H | OH | OH | Cbz—NH— | >300 | 250 | 24 (10 po) | 1 (10 sc) |
| | | | | | | | | | 10 (30 po) |
| CH₃SO₂NH | cyclohexyl | H | OH | CH₃O | NH₂ | — | — | — | 4 (10 sc) |
| | | | | | | | | | 0 (30 po) |
| CH₃SO₂NH | cyclohexyl | H | OH | OH | NH₂ | >300 | 121 | 18 (10 po) | — |
| CH₃SO₂NH | cyclopropyl, H (isomer A) | | OH | OH | NH₂ | 40 | 15 | 3 (10 po) | 30 (10 sc) |
| | | | | | | | | | 2 (30 po) |
| CH₃SO₂NH | cyclopropyl, H (isomer B) | | OH | OH | NH₂ | >300 | 300 | 17 (10 po) | — |

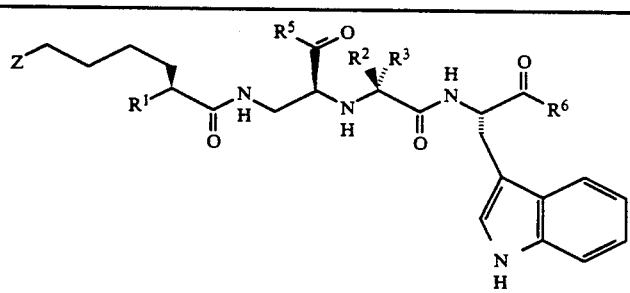

| R¹ | R² | R³ | R⁵ | R⁶ | Z | IC₅₀, nM NEP | ACE | Change in BP DOCA | FSHR |
|---|---|---|---|---|---|---|---|---|---|
| CH₃SO₂NH | i-Pr | H | OH | OH | NH₂ | | | | 5 (30 po) |

We claim:

1. A compound of the formula

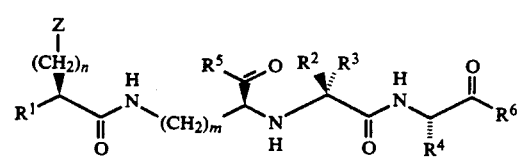

wherein

Z is amino, lower alkylamino, di-(lower alkyl)amino R⁹C(O)NH— or a guanidino group of the formula R¹¹R¹²NC(=NR¹³)N(R¹⁴)— or R¹¹R¹²NC(NR¹³R¹⁴)=N—, wherein R¹¹, R¹², R¹³ and R¹⁴ are independently hydrogen or alkyl, or wherein R¹¹ and R¹², or R¹³ and R¹⁴, taken together with the nitrogen atom to which they are attached, comprise a 5- or 6-membered ring;

R¹ is hydrogen or lower alkyl-SO₂—NH—;

R² is hydrogen, lower alkyl, cyclolower alkyl or benzyl; and R³ is hydrogen, lower alkyl or cyclolower alkyl; or R² and R³, together with the carbon to which they are attached, comprise a 3-7 membered carbocyclic ring;

R⁴ is hydrogen, lower alkyl, aryl lower alkyl or heteroaryllower alkyl, wherein the aryl portion of said aryl lower alkyl is a phenyl group and the heteroaryl portion of said heteroaryllower alkyl is an indolyl group, and said phenyl or indolyl groups are substituted by 0 to 1 substituents selected from hydroxy, lower alkoxy or loweralkyl sulfonamido;

$R^9$ is lower alkyl, lower alkoxy, aryllower alkoxy wherein the aryl portion of said aryllower alkoxy is a phenyl group, amino, alkylamino or dialkylamino;

n is 4;

m is 1; and $R^5$ and $R^6$ are independently selected from the group consisting of hydroxy, lower alkoxy or aryllower alkoxy wherein the aryl portion of said aryllower alkoxy is a phenyl group;

or a pharmaceutically acceptable addition salt thereof.

2. A compound of claim 1 wherein $R^4$ is aryllower alkyl.

3. A compound of claim 2 wherein $R^4$ is 4-hydroxyphenylmethyl or 3-methanesulfonylamidophenylmethyl.

4. A compound of claim 2 wherein: Z is selected from the group consisting of amino, $R^9C(O)NH-$ and $R^{11}R^{12}NC(=NR^{13})N(R^{14})-$, wherein $R^9$ is aryllower alkoxy, $R^{11}$ and $R^{13}$ are alkyl, and $R^{12}$ and $R^{14}$ are hydrogen; and $R^1$ is H or lower alkyl-$SO_2$—NH—.

5. A compound of claim 4 wherein Z is amino, benzyloxycarbonylamino or $C_2H_5NC(=NC_2H_5)NH-$.

6. A compound of claim 4 wherein $R^3$ is hydrogen and $R^2$ is aryllower alkyl, cyclolower alkyl or lower alkyl.

7. A compound of claim 6 wherein $R^2$ is methyl, iso-propyl, n-propyl, benzyl, cyclopropyl, cyclobutyl, cyclopentyl or cyclohexyl.

8. A compound of claim 4 wherein $R^2$ and $R^3$, together with the carbon to which they are attached, comprise a 3–6 membered carbocyclic ring.

9. A compound of claim 1 having the structural formula

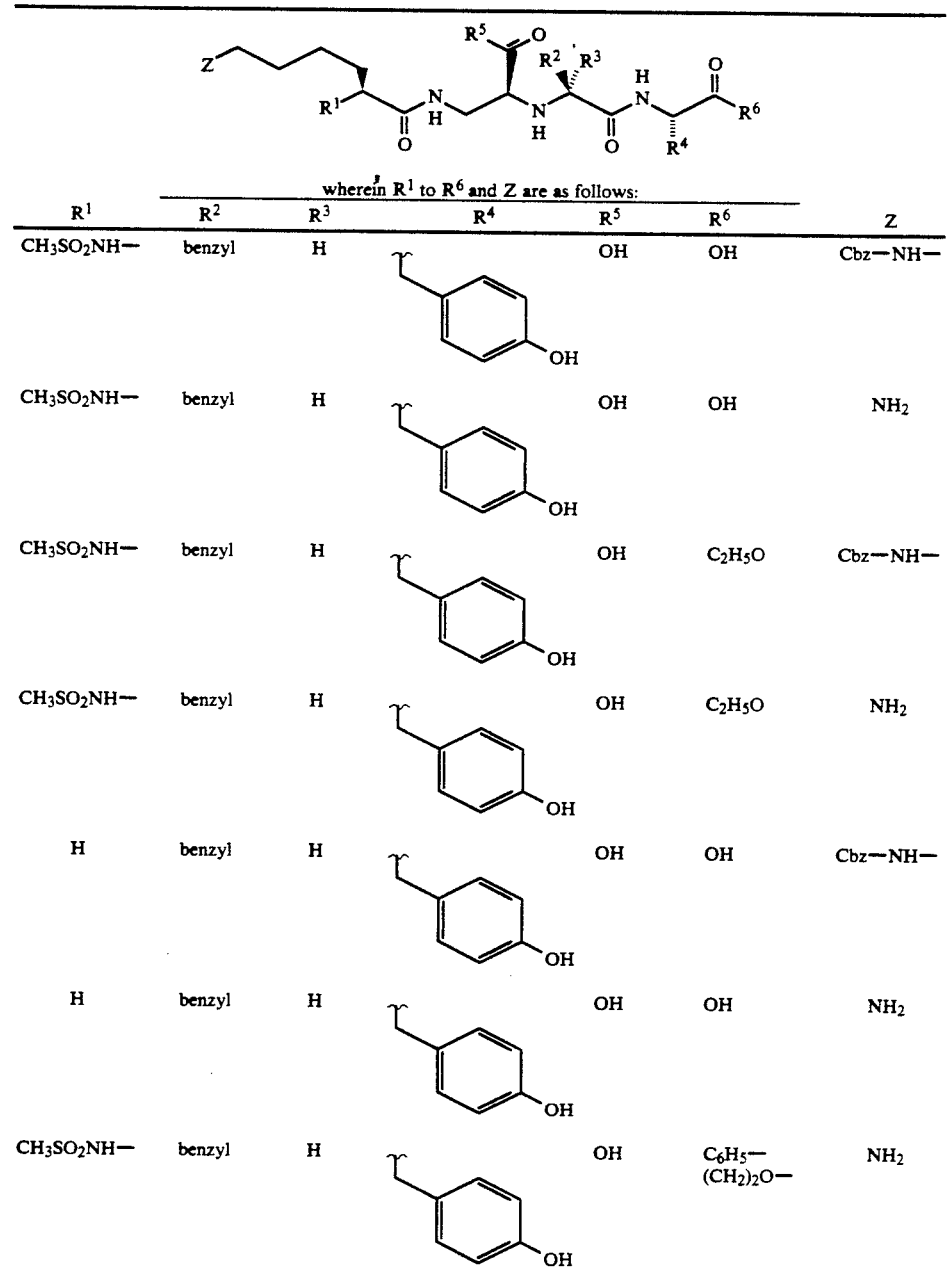

-continued

| | | | | | | |
|---|---|---|---|---|---|---|
| CH$_3$SO$_2$NH— | benzyl | H | 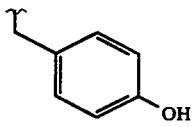 4-hydroxybenzyl | C$_2$H$_5$O | OH | Cbz—NH— |
| CH$_3$SO$_2$NH— | benzyl | H | 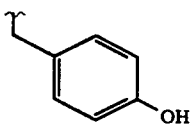 4-hydroxybenzyl | C$_2$H$_5$O | OH | NH$_2$ |
| CH$_3$SO$_2$NH— | benzyl | H | 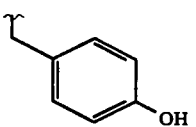 4-hydroxybenzyl | C$_6$H$_5$—(CH$_2$)$_2$O | OH | Cbz—NH— |
| CH$_3$SO$_2$NH— | benzyl | H | 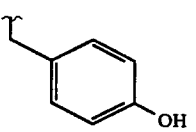 4-hydroxybenzyl | C$_6$H$_5$—(CH$_2$)$_2$O | OH | NH$_2$ |
| CH$_3$SO$_2$NH— | benzyl | H | 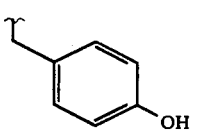 4-hydroxybenzyl | C$_6$H$_5$—(CH$_2$)$_2$O | CH$_3$O | NH$_2$ |
| CH$_3$SO$_2$NH— | benzyl | H | 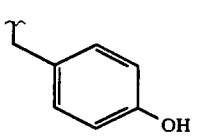 4-hydroxybenzyl | CH$_3$O | CH$_3$O | NH$_2$ |
| CH$_3$SO$_2$NH— | benzyl | H | 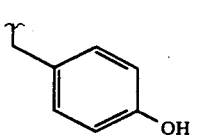 4-hydroxybenzyl | C$_6$H$_5$—(CH$_2$)$_2$O | CH$_3$O | Cbz—NH— |
| CH$_3$SO$_2$NH— | benzyl | H | 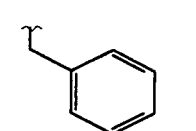 3-(CH$_3$SO$_2$NH)benzyl | C$_2$H$_5$O | C$_2$H$_5$O | NH$_2$ |
| CH$_3$SO$_2$NH— | benzyl | H | 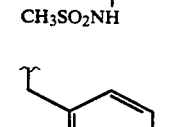 3-(CH$_3$SO$_2$NH)benzyl | OH | OH | NH$_2$ |
| CH$_3$SO$_2$NH— | benzyl | H | 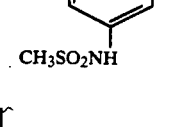 4-hydroxybenzyl | OH | OH | 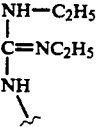 |
| CH$_3$SO$_2$NH— | i-C$_3$H$_7$ | H | 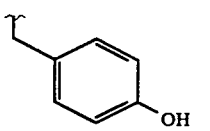 4-hydroxybenzyl | OH | OH | Cbz—NH— |

-continued

| | | | | | | |
|---|---|---|---|---|---|---|
| CH$_3$SO$_2$NH— | i-C$_3$H$_7$ | H | 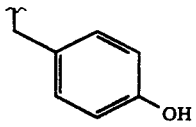 | OH | OH | NH$_2$ |
| CH$_3$SO$_2$NH— | i-C$_3$H$_7$ | H | 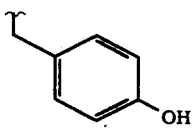 | CH$_3$O | OH | Cbz—NH— |
| CH$_3$SO$_2$NH— | i-C$_3$H$_7$ | H | 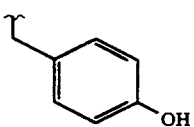 | CH$_3$O | OH | NH$_2$ |
| CH$_3$SO$_2$NH— | n-C$_3$H$_7$ | H | 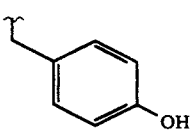 | OH | CH$_3$O | Cbz—NH— |
| CH$_3$SO$_2$NH— | n-C$_3$H$_7$ | H | 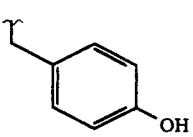 | OH | CH$_3$O | NH$_2$ |
| CH$_3$SO$_2$NH— | n-C$_3$H$_7$ | H | 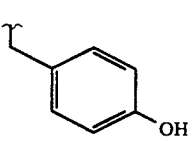 | OH | OH | NH$_2$ |
| CH$_3$SO$_2$NH— | n-C$_3$H$_7$ | H | 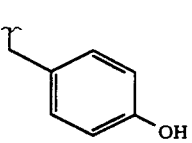 | OH | OH | Cbz—NH— |
| CH$_3$SO$_2$NH— | n-C$_3$H$_7$ | H | 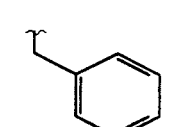 | OH | C$_2$H$_5$O | Cbz—NH— |
| CH$_3$SO$_2$NH— | n-C$_3$H$_7$ | H | 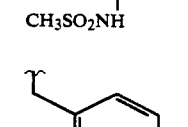 | OH | C$_2$H$_5$O | NH$_2$ |
| CH$_3$SO$_2$NH— | n-C$_3$H$_7$ | H | 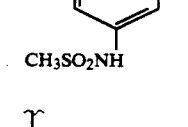 | OH | OH | NH$_2$ |
| CH$_3$SO$_2$NH— | CH$_3$ | H | 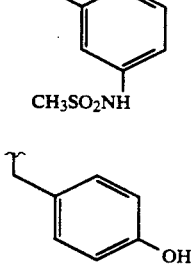 | OH | OH | NH$_2$ |

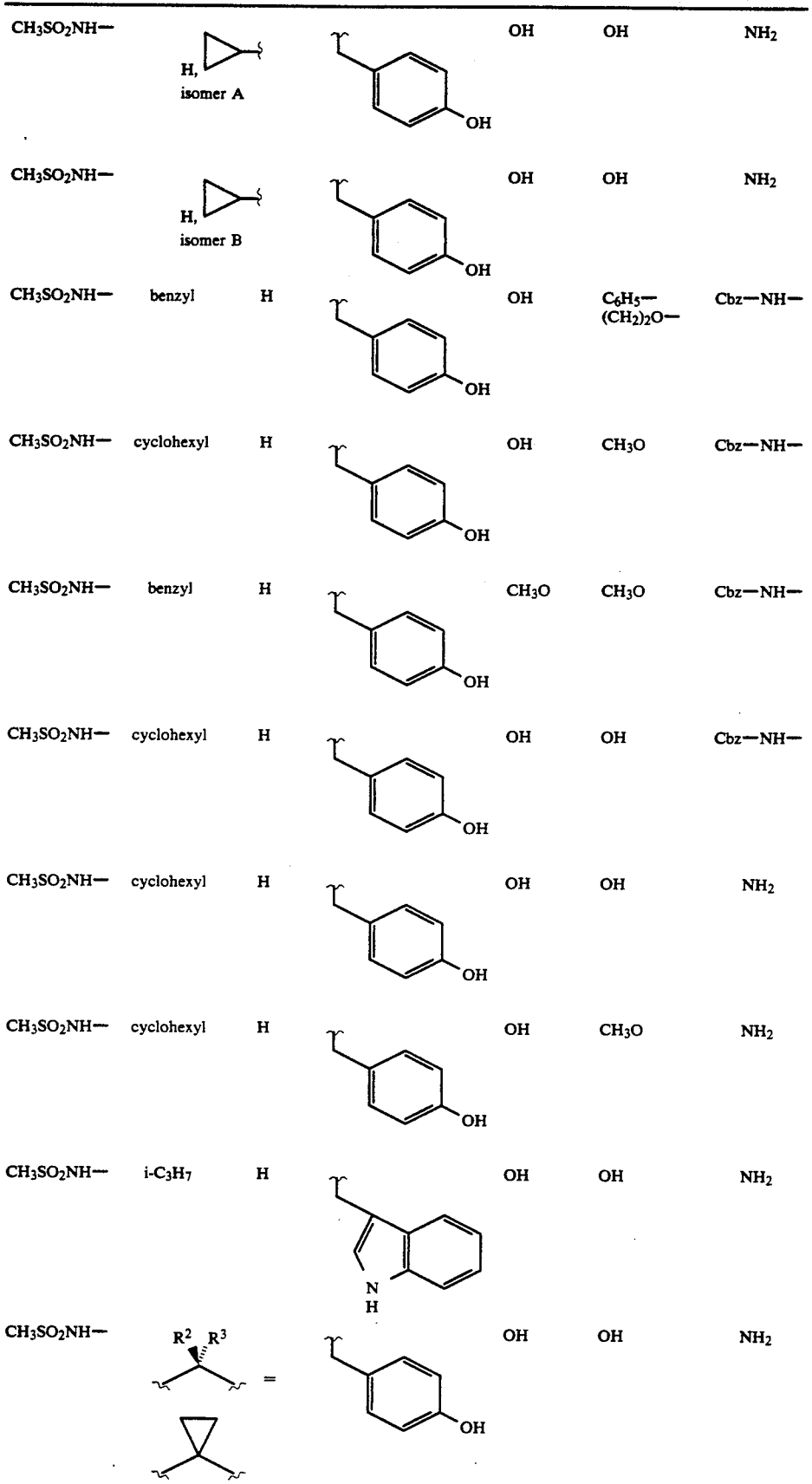

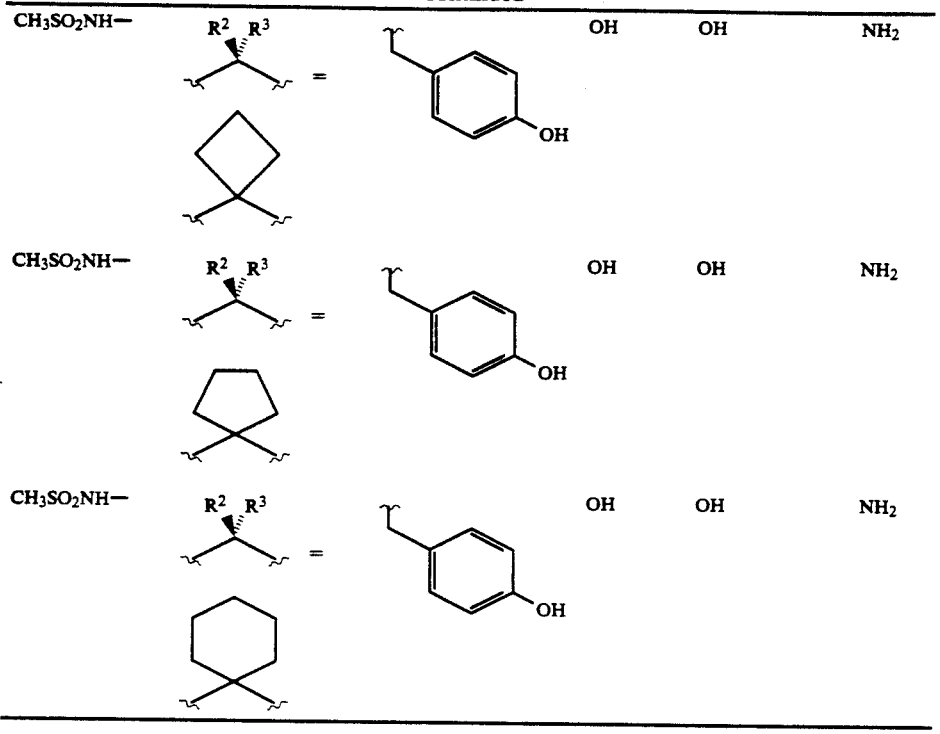
10. A pharmaceutical composition useful for treating hypertension, congestive heart failure or renal insufficiency comprising an effective amount of a compound of claim 2 in a pharmaceutically acceptable carrier.
11. A method of treating hypertension comprising administering to a mammal in need of such treatment a pharmaceutical composition of claim 10.
* * * * *

UNITED STATES PATENT AND TRADEMARK OFFICE
CERTIFICATE OF CORRECTION

PATENT NO. : 5,298,492

DATED : MARCH 29, 1994

INVENTOR(S) : BERNARD R. NEUSTADT, ET AL.

It is certified that error appears in the above-identified patent and that said Letters Patent is hereby corrected as shown below:

```
In claim 10, column 65, line 34, delete "claim 2", and insert
in place therefor --claim 1--.
```

Signed and Sealed this

Nineteenth Day of July, 1994

Attest:

BRUCE LEHMAN

Attesting Officer     Commissioner of Patents and Trademarks